(12) United States Patent
Hossainy et al.

(10) Patent No.: US 8,173,199 B2
(45) Date of Patent: May 8, 2012

(54) 40-O-(2-HYDROXY)ETHYL-RAPAMYCIN COATED STENT

(75) Inventors: Syed F. A. Hossainy, Fremont, CA (US); Gordon Stewart, San Francisco, CA (US); Mark A. Williams, Redwood City, CA (US); Jeff Royal, San Francisco, CA (US); Paul M. Consigny, San Jose, CA (US); Dorrie M. Happ, Madison, WI (US); Kurt Scheinpflug, Sunnyvale, CA (US); Ty Hu, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 337 days.

(21) Appl. No.: 11/527,893

(22) Filed: Sep. 26, 2006

(65) Prior Publication Data
US 2007/0020381 A1    Jan. 25, 2007

Related U.S. Application Data

(62) Division of application No. 10/108,004, filed on Mar. 27, 2002.

(51) Int. Cl.
*A61L 33/00* (2006.01)
*B05D 3/02* (2006.01)
*A61F 2/06* (2006.01)

(52) U.S. Cl. .... 427/2.24; 427/2.1; 427/2.25; 427/372.2; 623/1.11; 623/1.42; 623/1.44; 623/1.46

(58) Field of Classification Search .......... 427/2.1, 427/2.24
See application file for complete search history.

(56) References Cited

U.S. PATENT DOCUMENTS

| | | | |
|---|---|---|---|
| 2,072,303 A | | 3/1937 | Herrmann et al. |
| 2,386,454 A | | 10/1945 | Frosch et al. |
| 3,773,737 A | | 11/1973 | Goodman et al. |
| 3,849,514 A | | 11/1974 | Gray, Jr. et al. |
| 3,929,992 A | | 12/1975 | Sehgal et al. |
| 4,151,413 A | | 4/1979 | Arnold |
| 4,226,243 A | | 10/1980 | Shalaby et al. |
| 4,316,885 A | | 2/1982 | Rakhit |
| 4,325,903 A | | 4/1982 | Wissbrun et al. |
| 4,329,383 A | | 5/1982 | Joh |
| 4,343,931 A | | 8/1982 | Barrows |
| 4,395,538 A | * | 7/1983 | Taira et al. .................. 528/272 |
| 4,459,252 A | | 7/1984 | MacGregor |
| 4,529,792 A | | 7/1985 | Barrows |

(Continued)

FOREIGN PATENT DOCUMENTS

DE    42 24 401    1/1994

(Continued)

OTHER PUBLICATIONS

Anonymous, *Rolling Therapeutic Agent Loading Device for Therapeutic Agent Delivery or Coated Stent* (Abstract 434009), Res. Disclos. p. 975 (Jun. 2000).

(Continued)

*Primary Examiner* — Timothy Meeks
*Assistant Examiner* — Cachet Sellman
(74) *Attorney, Agent, or Firm* — Squire Sanders (US) LLP

(57) ABSTRACT

A method and coating for reducing the release rate of an active agent from an implantable device, such as a stent, is disclosed.

4 Claims, 4 Drawing Sheets

U.S. PATENT DOCUMENTS

| | | |
|---|---|---|
| 4,611,051 A | 9/1986 | Hayes et al. |
| 4,650,803 A | 3/1987 | Stella et al. |
| 4,656,242 A | 4/1987 | Swan et al. |
| 4,733,665 A | 3/1988 | Palmaz |
| 4,800,882 A | 1/1989 | Gianturco |
| 4,865,846 A * | 9/1989 | Kaufman ................... 424/428 |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,059,211 A | 10/1991 | Stack et al. |
| 5,100,883 A | 3/1992 | Schiehser |
| 5,100,992 A | 3/1992 | Cohn et al. |
| 5,102,876 A | 4/1992 | Caufield |
| 5,112,457 A | 5/1992 | Marchant |
| 5,114,718 A * | 5/1992 | Damani ................... 424/422 |
| 5,118,677 A | 6/1992 | Caufield |
| 5,118,678 A | 6/1992 | Kao et al. |
| 5,120,725 A | 6/1992 | Kao et al. |
| 5,120,727 A | 6/1992 | Kao et al. |
| 5,120,842 A | 6/1992 | Failli et al. |
| 5,133,742 A | 7/1992 | Pinchuk |
| 5,138,051 A | 8/1992 | Hughes et al. |
| 5,151,413 A | 9/1992 | Caufield et al. |
| 5,162,333 A | 11/1992 | Failli et al. |
| 5,163,952 A | 11/1992 | Froix |
| 5,165,919 A | 11/1992 | Sasaki et al. |
| 5,169,851 A | 12/1992 | Hughes et al. |
| 5,219,980 A | 6/1993 | Swidler |
| 5,221,740 A | 6/1993 | Hughes |
| 5,258,020 A | 11/1993 | Froix |
| 5,258,389 A | 11/1993 | Goulet et al. |
| 5,272,012 A | 12/1993 | Opolski |
| 5,273,760 A * | 12/1993 | Oshlack et al. ................ 424/480 |
| 5,292,516 A | 3/1994 | Viegas et al. |
| 5,298,260 A | 3/1994 | Viegas et al. |
| 5,300,295 A | 4/1994 | Viegas et al. |
| 5,306,286 A | 4/1994 | Stack et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,344,833 A | 9/1994 | Hughes |
| 5,380,299 A | 1/1995 | Fearnot et al. |
| 5,383,928 A | 1/1995 | Scott et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,468,253 A | 11/1995 | Bezwada et al. |
| 5,480,599 A | 1/1996 | Leven et al. |
| 5,485,496 A | 1/1996 | Lee et al. |
| 5,516,881 A | 5/1996 | Lee et al. |
| 5,527,337 A | 6/1996 | Stack et al. |
| 5,527,907 A | 6/1996 | Or et al. |
| 5,569,463 A | 10/1996 | Helmus et al. |
| 5,575,818 A | 11/1996 | Pinchuk |
| 5,578,073 A | 11/1996 | Haimovich et al. |
| 5,583,139 A | 12/1996 | Or et al. |
| 5,584,877 A | 12/1996 | Miyake et al. |
| 5,601,889 A | 2/1997 | Chundury et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,651,174 A | 7/1997 | Schwartz et al. |
| 5,658,995 A | 8/1997 | Kohn et al. |
| 5,665,772 A | 9/1997 | Cottens et al. |
| 5,667,767 A | 9/1997 | Greff et al. |
| 5,670,558 A | 9/1997 | Onishi et al. |
| 5,672,605 A | 9/1997 | Or et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,707,867 A | 1/1998 | Glenn |
| 5,711,958 A | 1/1998 | Cohn et al. |
| 5,713,949 A | 2/1998 | Jayaraman |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,766,710 A | 6/1998 | Turnlund et al. |
| 5,769,883 A | 6/1998 | Buscemi et al. |
| 5,776,184 A | 7/1998 | Tuch |
| 5,783,657 A | 7/1998 | Pavlin et al. |
| 5,788,979 A | 8/1998 | Alt et al. |
| 5,795,318 A | 8/1998 | Wang et al. |
| 5,798,355 A | 8/1998 | Steiner et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. ................... 604/49 |
| 5,837,008 A | 11/1998 | Berg et al. |
| 5,837,313 A | 11/1998 | Ding et al. ................... 427/2.21 |
| 5,843,172 A | 12/1998 | Yan |
| 5,843,960 A | 12/1998 | Steiner et al. |
| 5,846,981 A | 12/1998 | Steiner et al. |
| 5,849,859 A | 12/1998 | Acemoglu |
| 5,851,508 A | 12/1998 | Greff et al. ................... 424/9.411 |
| 5,858,746 A | 1/1999 | Hubbell et al. ............... 435/177 |
| 5,865,814 A | 2/1999 | Tuch ........................... 604/265 |
| 5,869,127 A | 2/1999 | Zhong ......................... 427/2.12 |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,897,911 A | 4/1999 | Loeffler ....................... 427/2.25 |
| 5,898,029 A | 4/1999 | Lyons et al. |
| 5,902,875 A | 5/1999 | Roby et al. |
| 5,905,168 A | 5/1999 | Dos Santos et al. |
| 5,910,564 A | 6/1999 | Gruning et al. |
| 5,912,253 A | 6/1999 | Cottens et al. |
| 5,914,387 A | 6/1999 | Roby et al. |
| 5,919,893 A | 7/1999 | Roby et al. |
| 5,925,720 A | 7/1999 | Kataoka et al. |
| 5,932,243 A | 8/1999 | Fricker et al. |
| 5,932,299 A | 8/1999 | Katoot |
| 5,955,509 A | 9/1999 | Webber et al. |
| 5,958,385 A | 9/1999 | Tondeur et al. |
| 5,962,007 A | 10/1999 | Cooper et al. |
| 5,962,138 A | 10/1999 | Kolluri et al. |
| 5,968,091 A | 10/1999 | Pinchuk |
| 5,971,954 A | 10/1999 | Conway et al. ................ 604/96 |
| 5,980,564 A | 11/1999 | Stinson |
| 5,980,928 A | 11/1999 | Terry ........................... 424/427 |
| 5,980,972 A | 11/1999 | Ding ............................ 427/2.24 |
| 5,985,890 A | 11/1999 | Cottens et al. |
| 5,997,517 A | 12/1999 | Whitbourne ................ 604/265 |
| 6,001,117 A | 12/1999 | Huxel et al. |
| 6,010,530 A | 1/2000 | Goicoechea ................... 623/1 |
| 6,011,125 A | 1/2000 | Lohmeijer et al. |
| 6,013,621 A | 1/2000 | Nishi et al. |
| 6,015,541 A | 1/2000 | Greff et al. ................... 424/1.25 |
| 6,015,815 A | 1/2000 | Mollison |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. ................... 525/54.1 |
| 6,054,553 A | 4/2000 | Groth et al. |
| 6,056,906 A | 5/2000 | Werneth et al. |
| 6,056,993 A | 5/2000 | Leidner et al. |
| 6,060,451 A | 5/2000 | DiMaio et al. ................ 514/13 |
| 6,060,518 A | 5/2000 | Kabanov et al. |
| 6,066,156 A | 5/2000 | Yan |

| Patent No. | Date | Inventor |
|---|---|---|
| 6,080,488 A | 6/2000 | Hostettler et al. ......... 428/423.3 |
| 6,083,534 A | 7/2000 | Wallach et al. |
| 6,096,070 A | 8/2000 | Ragheb et al. ................. 623/1 |
| 6,099,562 A | 8/2000 | Ding et al. ................. 623/1.46 |
| 6,100,346 A | 8/2000 | Jamiolkowski et al. |
| 6,110,188 A | 8/2000 | Narciso, Jr. ................. 606/153 |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,847 A | 9/2000 | Yang et al. |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,139,573 A | 10/2000 | Sogard et al. |
| 6,143,037 A | 11/2000 | Goldstein et al. |
| 6,143,354 A | 11/2000 | Koulik et al. |
| 6,153,252 A * | 11/2000 | Hossainy et al. ............. 427/2.3 |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,200,985 B1 | 3/2001 | Cottens et al. |
| 6,203,551 B1 | 3/2001 | Wu |
| 6,206,915 B1 | 3/2001 | Fagan et al. |
| 6,211,249 B1 | 4/2001 | Cohn et al. |
| 6,214,901 B1 | 4/2001 | Chudzik et al. |
| 6,221,102 B1 | 4/2001 | Baker et al. |
| 6,228,934 B1 | 5/2001 | Horowitz et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,273,913 B1 | 8/2001 | Wright et al. |
| 6,277,449 B1 | 8/2001 | Kolluri et al. |
| 6,281,225 B1 | 8/2001 | Hearst et al. |
| 6,283,947 B1 | 9/2001 | Mirzaee |
| 6,283,949 B1 | 9/2001 | Roorda |
| 6,284,305 B1 | 9/2001 | Ding et al. |
| 6,284,788 B1 | 9/2001 | Mittendorf et al. |
| 6,287,628 B1 | 9/2001 | Hossainy et al. |
| 6,293,959 B1 | 9/2001 | Miller et al. |
| 6,299,604 B1 | 10/2001 | Ragheb et al. |
| 6,306,176 B1 | 10/2001 | Whitbourne |
| 6,309,402 B1 | 10/2001 | Jendersee et al. |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,384,046 B1 | 5/2002 | Schuler et al. |
| 6,387,124 B1 | 5/2002 | Buscemi et al. |
| 6,387,379 B1 | 5/2002 | Goldberg et al. |
| 6,395,326 B1 | 5/2002 | Castro et al. |
| 6,406,739 B1 | 6/2002 | LeBoeuf et al. |
| 6,419,692 B1 | 7/2002 | Yang et al. |
| 6,451,373 B1 | 9/2002 | Hossainy et al. |
| 6,475,235 B1 | 11/2002 | Jayaraman |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,547,819 B2 | 4/2003 | Strecker |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,574,497 B1 | 6/2003 | Pacetti |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Wu et al. |
| 6,623,448 B2 | 9/2003 | Slater |
| 6,623,764 B1 | 9/2003 | Sokoll et al. |
| 6,625,486 B2 | 9/2003 | Lundkvist et al. |
| 6,645,135 B1 | 11/2003 | Bhat |
| 6,645,195 B1 | 11/2003 | Bhat et al. |
| 6,652,581 B1 | 11/2003 | Ding |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 * | 3/2004 | Hossainy et al. ............. 427/2.25 |
| 6,716,444 B1 | 4/2004 | Castro et al. |
| 6,723,120 B2 | 4/2004 | Yan |
| 6,733,768 B2 | 5/2004 | Hossainy et al. |
| 6,739,033 B2 | 5/2004 | Hijlkema et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 * | 6/2004 | Pacetti ......................... 428/212 |
| 6,758,859 B1 | 7/2004 | Dang et al. |
| 6,759,054 B2 | 7/2004 | Chen et al. |
| 6,764,505 B1 | 7/2004 | Hossainy et al. |
| 6,787,179 B2 * | 9/2004 | Timm et al. .................. 427/2.24 |
| 6,823,576 B2 | 11/2004 | Austin |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,899,731 B2 | 5/2005 | Li et al. |
| 6,948,223 B2 | 9/2005 | Shortt |
| 7,077,859 B2 * | 7/2006 | Sirhan et al. .................. 623/1.15 |
| 7,291,165 B2 | 11/2007 | Rosenthal et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0027340 A1 | 10/2001 | Wright et al. |
| 2001/0029351 A1 | 10/2001 | Falotico et al. |
| 2001/0031769 A1 | 10/2001 | Jackman et al. |
| 2001/0034344 A1 | 10/2001 | Mittendorf et al. |
| 2001/0037145 A1 | 11/2001 | Guruwaiya et al. |
| 2001/0046518 A1 | 11/2001 | Sawhney |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |

| | | | |
|---|---|---|---|
| 2002/0051730 A1* | 5/2002 | Bodnar et al. ............... 422/33 |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0082685 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0127263 A1* | 9/2002 | Carlyle et al. ............... 424/423 |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0039696 A1* | 2/2003 | Porter ............... 424/486 |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0144727 A1 | 7/2003 | Rosenthal et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0220665 A1 | 11/2004 | Hossainy et al. |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0113903 A1 | 5/2005 | Rosenthal et al. |
| 2005/0118344 A1 | 6/2005 | Pacetti |
| 2005/0119720 A1 | 6/2005 | Gale et al. |
| 2005/0233062 A1 | 10/2005 | Hossainy et al. |

FOREIGN PATENT DOCUMENTS

| | | |
|---|---|---|
| EP | 0 310 856 | 4/1989 |
| EP | 0 323 042 | 7/1989 |
| EP | 0 376 656 | 7/1990 |
| EP | 0 396 429 | 11/1990 |
| EP | 0 401 747 | 12/1990 |
| EP | 0 414 632 | 2/1991 |
| EP | 0 475 230 | 3/1992 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 875 218 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 978 288 | 2/2000 |
| EP | 0 982 041 | 3/2000 |
| EP | 1 023 879 | 8/2000 |
| EP | 1 036 562 | 9/2000 |
| EP | 1 064 942 | 1/2001 |
| EP | 1 192 957 | 4/2002 |
| EP | 1 273 314 | 1/2003 |
| JP | 11299901 | 11/1999 |
| JP | 2000-051367 | 2/2000 |
| JP | 2001-190687 | 7/2001 |
| JP | 2004-523275 | 8/2004 |
| JP | 2005-512959 | 5/2005 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 90/01969 | 3/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 95/31104 | 11/1995 |
| WO | WO 96/13273 | 5/1996 |
| WO | WO 96/40140 | 12/1996 |
| WO | WO 96/40174 | 12/1996 |
| WO | WO 97/03654 | 2/1997 |
| WO | WO 97/10011 | 3/1997 |
| WO | WO 97/31020 | 8/1997 |
| WO | WO 97/35575 | 10/1997 |
| WO | WO 97/45105 | 12/1997 |
| WO | WO 97/46590 | 12/1997 |
| WO | WO 98/02441 | 1/1998 |
| WO | WO 98/04256 | 2/1998 |
| WO | WO 98/08463 | 3/1998 |
| WO | WO 98/09523 | 3/1998 |
| WO | WO 98/10747 | 3/1998 |
| WO | WO 98/17331 | 4/1998 |
| WO | WO 98/23228 | 6/1998 |
| WO | WO 98/32398 | 7/1998 |
| WO | WO 98/36784 | 8/1998 |
| WO | WO 98/44921 | 10/1998 |

| WO | WO 98/44922 | 10/1998 |
| WO | WO 99/01118 | 1/1999 |
| WO | WO 99/16386 | 4/1999 |
| WO | WO 99/19471 | 4/1999 |
| WO | WO 99/19473 | 4/1999 |
| WO | WO 99/24036 | 5/1999 |
| WO | WO 99/38546 | 8/1999 |
| WO | WO 99/39720 | 8/1999 |
| WO | WO 99/42104 | 8/1999 |
| WO | WO 99/44584 | 9/1999 |
| WO | WO 99/44597 | 9/1999 |
| WO | WO 99/60997 | 12/1999 |
| WO | WO 99/61040 | 12/1999 |
| WO | WO 99/63981 | 12/1999 |
| WO | WO 00/02599 | 1/2000 |
| WO | WO 00/09085 | 2/2000 |
| WO | WO 00/12147 | 3/2000 |
| WO | WO 00/15208 | 3/2000 |
| WO | WO 00/18446 | 4/2000 |
| WO | WO 00/24390 | 5/2000 |
| WO | WO 00/32234 | 6/2000 |
| WO | WO 00/32238 | 6/2000 |
| WO | WO 00/33878 | 6/2000 |
| WO | WO 00/38590 | 7/2000 |
| WO | WO 00/38703 | 7/2000 |
| WO | WO 00/38754 | 7/2000 |
| WO | WO 00/42949 | 7/2000 |
| WO | WO 00/56247 | 9/2000 |
| WO | WO 00/57818 | 10/2000 |
| WO | WO 00/64506 | 11/2000 |
| WO | WO 00/66122 | 11/2000 |
| WO | WO 00/71052 | 11/2000 |
| WO | WO 00/74665 | 12/2000 |
| WO | WO 01/01890 | 1/2001 |
| WO | WO 01/01957 | 1/2001 |
| WO | WO 01/14387 | 3/2001 |
| WO | WO 01/15751 | 3/2001 |
| WO | WO 01/17577 | 3/2001 |
| WO | WO 01/23395 | 4/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 01/87373 | 11/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/035131 | 5/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2005/004945 | 1/2005 |

OTHER PUBLICATIONS

Barath et al., *Low Dose of Antitumor Agents Prevents Smooth Muscle Cell Proliferation After Endothelial Injury*; JACC 13(2):252A (Abstract) (Feb. 1989).
Dichek et al., *Seeding of Intravascular Stents with Genetically Engineered Endothelial Cells*, Circ. 80(5):1347-1353 (1989).
*Everolimus*, http://www.micromedex.com/products/drugdex/updates/evero.htm, printed Mar. 6, 2002 (12 pags).
*Guidant Licenses Everolimus From Novartis for Drug Eluting Stents* (Press Release, Mar. 27, 2002), http://biz.yahoo.com/bw/020327/272460_1.html, printed Mar. 29, 2002 (3 pages).
Herdeg et al., *Antiproliferative Stent Coatings: Taxol and Related Compounds*, Semin. Intervent. Cardiol. 3:197-199 (1998).
*KYNAR® and KYNAR®FLEX PVCF, The Base Resins for Demanding Industrial Applications*, http://www.atofinachemicals.com/kynarglobal/index.cfm, printed Mar. 7, 2002 (1 page).
Matsumaru et al., *Embolic Materials for Endovascular Treatment of Cerebral Lesions*; J. Biomater. Sci. Polymer Edn, 8(7):555-569 (1997).
Miyazaki et al., "*Antitumor Effect of Implanted Ethylene-Vinyl Alcohol Copolymer Matrices Containing Anticancer Agents on Ehrlich Ascites Carcinoma and P388 Leukemia in Mice*," Chem. Pharm. Bull., 33(6):2490-2498 (1985).
Miyazawa, et al.; *Effects of Pemirolast and Tranilast on Intimal Thickening After Arterial Injury in the Rat*; J. Cardiovasc. Pharmacol., pp. 157-162 (1997).
Ohsawa, et al.; *Preventive Effects of an Antiallergic Drug, Pemirolast Potassium, on Restenosis After Percutaneous Transluminal Coronary Angioplasty*, American Heart Journal; pp. 1081-1087 (Dec. 1998).
*International Nonproprietary Names for Pharmaceutical Substances (INN)*, WHO Drug Information 14(3):183, 184, 194 (2000) (3 pages).
Shigeno, *Prevention of Cerebrovascular Spasm by Bosentan, Novel Endothelin Receptor*, Chemical Abstract 125:212307 (1996).
*TECHSPRAY Product Information, HFE Flux Remover*, http://www.techspray.com/1686info.htm, printed Mar. 14, 2002 (2 pages).
*Transplant 2001: Certican (Everolimus) Effective in Preventing Acute Rejection in Renal Transplantation*, http://www.docguide.com/dg.nsf/PrintPrint/A9A24F321A71712485256A4E00689824, printed Mar. 6, 2002 (2 pages).
International Search Report and Written Opinion for PCT/US2004/017060, filed May 28, 2004, mailed Dec. 30, 2004, 7 pgs.
Notification of Reasons for Refusal issued by JPO on Nov. 17, 2009, in connection with Appl. No. 2003-579899, 4 pgs.
Translation of a Notification of Reasons for Refusal issued by JPO on Nov. 17, 2009, in connection with Appl. No. 2003-579899, 3 pgs.
Neuhaus et al., "mTOR Inhibitors: An Overview", Liver Transpl. vol. 7. No. 6, pp. 473-484.
Anonymous,*A Simple Approach for Glass Transition Temperature Prediction*, http://www.geocities.com/ResearchTriangle/Thinktank/4146/6400glass-temperature.html, printed May 5, 2005.(2 pages).
Anonymous, *Appendix I—Glass Transition Temperature*($T_g$) www.Dymax.com/pdf/SPIE-Paper-Apendix.pdf, printed May 9, 2005 (2 pages).
Anonymous, *Cardiologists Draw—Up The Dream Stent*, Clinica 710:15 (Jun. 17, 1996), http://www.dialoweb.com/cgi/document?req=1061848202959, printed Aug. 25, 2003 (2 pages).
Anonymous, *Differential Scanning Calorimetry*, http://www.pslc.ws/macrog/dsc.htm, printed May 9, 2005 (8 pages).
Anonymous, *Glass Transition Temperature*, http://isInotes.cps.nnsu.edu/trp/back/mol_glas.html, printed May 5, 2005 (1 page).
Anonymous, *Glass transition temperature*, http://palimpsest.stanford.edu/don/dt/dt1549.html, printed May 5, 2005 (1 page) .
Anonymous,*Heparin-coated stents cut complications by*30%, Clinica 732:17 (Nov. 18, 1996), http: //www.dialogweb.com/cgi/document?reg=1061847871753, printed Aug. 25, 2003 (2 pages).
Anonymous, *How Big are Polymers?* www.chemeng.ucla.edu/che112/Notes, printed May 9, 2005 (13 pages).
Anonymous,*Measuring and Understanding Tg (Glass Transition Temperature)* , Arlon, Application Notes (4 pages).
Anonymous,*Stenting continues to dominate cardiology*, Clinica 720:22 (Sep. 2, 1996), http://www.dialogweb.com/cgi/document?req=1061848017752, printed Aug. 25, 2003 (2 pages).
Anonymous, *The Glass Transition*, http://www.pslc.ws/macrog/tg.htm, printed May 18, 2005 (11 pages).
Anonymous, *Thermoplastics —An Introduction*, http://www.azom.com/details.asp?Article1D+83&head=Thermoplastics%2B-%2BAn%2BIntroduction, printed May 18, 2005 (5 pages).
Aoyagi et al., *Preparation of cross-linked aliphatic polyester and application to thermo-responsive material*, Journal of Controlled Release 32:87-96 (1994).
Arvanitoyannis et al., *Novel star-shaped polylactide with glycerol using stannous octoate or tetraphenyl tin as catalyst: 1 Synthesis, characterization and study of their biodegradability*, Polymer vol. 36, No. 15, pp. 2947-2956 (1995).
Baird et al, *Dielectric behaviour and morphology of polyvinylidene fluoride*, Journal of Material Science 10:1248-1251 (1975).
Barbucci et al.,*Coating of commercially available materials with a new heparinizable material*, J. Biomed. Mater. Res. 25:1259-1274 (Oct. 1991).

Birmingham Polymers, Inc.,*Biodegradation Information*, http://www.birminghampolymers.com/htdocs/biodegradation.htm. printed Apr. 26, 2004 (2 pages).
Birmingham Polymers, Inc., *Chemical Properties of Selected Polymers*http://www.birminghampolymers.com/htdocs/Chemical Properties.htm, printed May 19, 2005 (2 pages).
Birmingham Polymers, Inc., *DLPLA IV vs. Mw*, http://www.birminghampolymers.com/htdocs/dlpla.htm. printed Apr. 26, 2004 (1 page).
Birmingham Polymers, Inc. *Physical Properties of Selected Polymers*, http://www.birminghampolymers.com/htdocs/physical_properties.htm, printed Apr. 26, 2004 (2 pages).
Birmingham Polymers, Inc., Standard Products, http://www.birminqhampolymers.com/htdocs/Standard_Products.htm, printed Apr. 26, 2004 (2 pages).
Black et al., *Glass Transitions of Some Block Copolymers*, Journal of Applied Polymer Science 18:2307-2310 (1974).
Bliznyuk et al., *Surface Glass Transition Temperature of Amorphous Polystyrene Measured by SFM*, pp. 1-5.
Bloembergen et al.,*Studies of Composition and Crystallinity of Bacterial Poly(β-hydroxybutyrate-co-β-hydroxyvalerate)*, Macromolecules 19, pp. 2865-2871 (1986).
Buchholz et al., *Cooling rate dependence of the glass transition temperature of polymer melts: Molecular dynamics study*, Journal of Chemical Physics 117(15):7364-7372 (Oct. 15, 2002).
Chung et al., *Inner core segment design for drug delivery control of thermo-responsive polymeric micelles*, Journal of Controlled Release 65:93-103 (2000).
Notification of Refusal issued by JPO on Aug. 3, 2010, in connection with Appl. No. 2003-579899, 1 pg.
Complete Translation of the Notification of Reasons for Refusal issued by JPO on Nov. 17, 2009, in connection with Appl. No. 2003-579899, 8 pgs.
Examination Report by EPO on Oct. 5, 2007, in connection with Appl. No. EP 03 745 538.3, 6 pgs.
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Ding et al., *Novel Synthesis of Poly(p-phenylene sulfide)from Cyclic Disulfide Oligomers*, Macromolecules 29:4811-4812 (1996).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Eling et al., *Biodegradable materials of poly(L-lactic acid): 1. melt-spun and solution-spun fibres*, Polymer, vol. 23, pp. 1587-1593 (1982).
EPO Examination Report for application 04 812 597.5-2307, mailed Feb. 26, 2007, 2 pgs.
EPO Examination Report for application 04 812 597.5-2307, mailed Sept. 6, 2007, 3 pgs.
EPO Examination Report for application 04 812 597.5-2307, mailed July 4, 2008, 3 pgs.
European Search Report for 05780079.9-2107, mailed Jan. 17, 2008, 6 pages.
Fernandez-Martin et al., *Glass Transition Temperature and Heat Capacity of Heterotacticlike PMMA*, Journal of Polymer Science: Polymer Physics Edition 19:1353-1363 (1981).
Forrest et al., *Effect of Free Surfaces on the Glass Transition Temperature of Thin Polymer Films*, Physical Review Letters 77(10):2002-2005 (Sep. 2, 1996).
Fryer et al., *Dependence of the Glass Transition Temperature of Polymer Films on Interfacial Energy and Thickness*, Macromolecules 34(16):5627-5634 (2001).
Fujii et al., *Investigation of the Stereoregularity of Poly(vinyl Alcohol)*, Journal of Polymer Science: Part A 2:2327-2347 (1964).
Gabriele Perego, Tiziano Vercellio, Copolymers of L and D, L Lactide with 6-caprolactone: synthesis and characterization, Malromol. Chem. 194, 2463-2469 (1993).
Gee et al., *The effect of ionizing radiation on the thermal properties of linear high polymers: Part 2. Nylon-6*, pp. 192-197 (1970).

Grohens et al., *Tacticity and surface chemistry effects on the glass transition temperature of thin supported PMMA films*, Mat. Res. Soc. Symp. 629:FF1.7.1-FF1.7.7 (2000).
*Guidant Licenses Everolimus From Novartis for Drug Eluting Stents* (Press Release, Mar. 27, 2002), http://biz.yahoo.com/bw/020327/272460_1.html, printed March 27, 2002 (2 pages).
Helmus, *Overview of Biomedical Materials*, MRS Bulletin, pp. 33-38 (1991).
Inoue et al., *An AB block copolymer of oligo(methyl methacrylate)and poly(acrylic acid)for micellar delivery of hydrophobic drugs*, Journal of Controlled Release 51:221-229 (1998).
International Search Report and Written Opinion for PCT/US2004/017060, filed May 28, 2004, mailed Dec. 30, 2004, 10 pgs.
International Search Report and Written Opinion for PCT/US2004/040121, filed Nov. 30, 2004, mailed Apr. 12, 2005, 12 pgs.
International Search Report for PCT/US2005/018579 filed May 26, 2005, mailed May 24, 2006, 16 pages.
Jacobsen et al., *Filling of Poly(Lactic Acid)With Native Starch*, Polymer Engineering and Science, vol. 36, No. 22, pp. 2799-2804 (1996).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid) α,ω-Alkylene Diesters, and Aliphatic Dicarbolic Acids*, Journal of Polymer Science, Part A: Polymer Chemistry, 37(4), 391-407 (1999).
*KYNAR® and KYNAR® FLEX PVDF, The Base Resins for Demanding Industrial Applications*, http://www.products.arkemagroup.com/print.cfm, printed May 18, 2005 (3 pages).
Lam et al., *Biodegradation of porous versus non-porous poly(L-lactic acid)films*, J. of Materials Science: Materials Medicine 5, pp. 181-189 (1994).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Löfgren et al., *Synthesis and Characterization of Biodegradable Homopolymers and Block Copolymers Based on 1,5-Dioxepan-2-one*, Macromolecules 27:5556-5562 (1994).
Lotz, *Phase Transitions and Structure of Crystalline Polymers*, pp. 1-27.
Marconi et al., *Covalent bonding of heparin to a vinyl copolymer for biomedical applications*, Biomaterials 18(12):885-890 (1997).
Micoulaut et al., *Glass Transition temperature variation, cross-linking and structure in network glasses: A stochastic approach*, Europhysics Letters 47(5):568-574 (1999).
Migliaresi et al., *Dynamic Mechanical and Calorimetric Analysis of Compression-Molded PLLA of Different Molecular Weights: Effect of Thermal Treatments*, J. of Applied Polymer Science, vol. 43, pp. 83-95 (1991).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nijenhuis et al.,*Highly crystalline as-polymerized poly(L-lactide)*, Polymer bulletin 26, pp. 71-77 (1991).
Nordrehaug et al., *A novel biocompatible coating applied to coronary stents*, European Heart Journal 14, p. 321 (P1694), Abstr. Suppl. (1993).
Ozaki et al., *New Stent Technologies*, Progress in Cardiovascular Diseases, vol. XXXIX(2):129-140 (Sep./Oct. 1996).
Parravicini et al., *Crystallization of Poly(Ethylene Terephthalate) (PET)from the Oriented Mesomorphic Form*, pp. 875-885 (1994).
Pechar et al., *Poly(ethylene glycol)Multiblock Copolymer as a Carrier of Anti-Cancer Drug Doxorubicin*, Bioconjugate Chemistry 11(2):131-139 (Mar./Apr. 2000).
Peng et al., *Role of polymers in improving the results of stenting in coronary arteries*, Biomaterials 17:685-694 (1996).

Reeve et al., *Polylactide Stereochemistry:Effect on Enzymatic Degradability*, Macromolecules 27, pp. 825-831 (1994).

Rogers et al., *Glass Formation in Polymers. I. The Glass Transitions of the Poly-(n-Alkyl Methacrylates)*, 61:985-990 (Jul. 1957).

Saotome, et al., *Novel Enzymatically Degradable Polymers Comprising α-Amino Acid, 1,2-Ethanediol, and Adipic Acid*, Chemistry Letters, pp. 21-24, (1991).

Sarasua et al., *Crystallization and Melting Behavior of Polylactides*, Macromolecules 31, pp. 3895-3905 (1998).

Scott et al., *Ehtylene-Vinyl Acetate Semi-Batch Emulsion Copolymerization: Use of Factorial Experiments for Process Optimization*, pp. 539-555 (1993).

Sichina, *Characterization of Polymers by TMA*, Perkin Elmer Polymers technical note (9 pages).

Sun et al., *Novel Copolyesters Containing Naphthalene Structure. I. From Bis(hydroxyalkyl)naphthalate and Bis[4-(2-hydroxyethoxyl)aryl] Compounds*, Journal of Polymer Science: Part A: Polymer Chemistry 34:1783-1792 (1996).

Taylor et al., *An Applied Approach to Film Formation: The glass transition temperature evolution of plasticized latex films*, downloaded May 5, 2005 (13 pages).

Translation of Notification of Refusal issued by JPO on Aug. 3, 2010, in connection with Appl. No. 2003- 579899, 1 pg.

Tsige et al., *Simulation study of the glass transition temperature in poly(methyl methacrylate)*, Physical Review E vol. 65: (2002) (8 pages).

van Beusekom et al., *Coronary stent coatings*, Coronary Artery Disease 5(7): 590-596 (Jul. 1994).

Van de Velde et al. Biopolymers; overview of several properties and consequences on their applications. Polymer Testing vol. 21 (2002) pp. 433-442.

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

40-O-(2-HYDROXY)ETHYL-RAPAMYCIN COATED STENT

CROSS REFERENCE TO RELATED APPLICATIONS

The present application is a divisional application of U.S. patent application Ser. No. 10/108,004, filed on Mar. 27, 2002, the teachings of which are incorporated herein in their entirety.

BACKGROUND OF THE INVENTION

1. Field of the Invention

The invention relates to drug eluting implantable devices, one example of which is a stent. More particularly, the invention relates to sustained delivery of 40-O-(2-hydroxy)ethyl-rapamycin from a stent.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to remodel the vessel wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Vasospasms and recoil of the vessel wall also threaten vessel closure. Moreover, thrombosis and restenosis of the artery may develop over several months after the procedure, which may necessitate another angioplasty procedure or a surgical by-pass operation. To reduce the partial or total occlusion of the artery by the collapse of arterial lining and to reduce the chance of the development of thrombosis and restenosis, an expandable, intraluminal prosthesis, also known as a stent, is implanted in the lumen to maintain the vascular patency.

Stents act as scaffoldings, functioning to physically hold open and, if desired, to expand the wall of the passageway. Typically, stents are capable of being compressed so that they can be inserted through small lumens via catheters and then expanded to a larger diameter once they are at the desired location. Mechanical intervention via stents has reduced the rate of restenosis as compared to balloon angioplasty. Yet, restenosis is still a significant clinical problem with rates ranging from 20-40%. When restenosis does occur in the stented segment, its treatment can be challenging, as clinical options are more limited as compared to lesions that were treated solely with a balloon.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method of medicating stents involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A potential shortcoming of the foregoing method of medicating stents is that the release rate of the therapeutic substance may be too high to provide an efficacious treatment. This shortcoming may be especially pronounced with certain therapeutic substances. For instance, it has been found that the release rate of 40-O-(2-hydroxy)ethyl-rapamycin from a standard polymeric coating is greater than 50% in about 24 hours. Thus, there is a need for a coating that reduces the release rate of 40-O-(2-hydroxy)ethyl-rapamycin in order to provide a more efficacious release rate profile. The present invention provides a coating to meet this need.

SUMMARY

In accordance with one aspect of the invention, a stent is disclosed including a radially expandable body and a coating covering at least a portion of the body, the coating having 40-O-(2-hydroxy)ethyl-rapamycin, or an analog or derivative thereof, wherein the release rate of the 40-O-(2-hydroxy)ethyl-rapamycin, or the analog or derivative thereof, in 24 hours after the implantation of the stent is less than about 50% of the total amount contained in the coating.

In accordance with a further aspect of the present invention, a method of inhibiting or eliminating the development of restenosis following a stent placement procedure is disclosed including implanting a stent which can elude 40-O-(2-hydroxy)ethyl-rapamycin, or an analog or derivative thereof, at a release rate of less than 50% of the total amount of the drug carried by the stent in a 24 hour period following the implantation procedure.

In a further aspect, a method of providing drug delivery capability for a stent is disclosed including coating a stent with a polymer containing 40-O-(2-hydroxy)ethyl-rapamycin, or analog or derivative thereof, wherein the coating has an in vivo release rate of less than 50% of the total amount of the 40-O-(2-hydroxy)ethyl-rapamycin, or analog or derivative thereof, in a 24 hour period.

In yet another aspect of the present invention, a method of treating a polymeric coating on a stent to reduce the rate of release of the drug from the coating is disclosed including exposing the coating to a temperature of a sufficient degree to cause modifications in the structure of the polymer which allows for the reduction of the release rate of the drug through the polymer.

Also disclosed, in another aspect, is a method of treating a coated stent containing a therapeutic substance to reduce the rate of release of the therapeutic substance from the coating including subjecting the coating to a stimuli so as to change the property of at least a region of the coating such that the change of the property of the region of the coating causes the therapeutic substance to be released more slowly from the region that has the changed property.

In another aspect of the present invention, a method of preparing a coated stent containing 40-O-(2-hydroxy)ethyl-rapamycin, or analog or derivative thereof, for an implantation procedure is disclosed including sterilizing the stent while maintaining the peak purity of the 40-O-(2-hydroxy) ethyl-rapamycin, or analog or derivative thereof, at a level greater than 90%.

DETAILED DESCRIPTION

Forming an Active Ingredient-Containing Coating

Figure 1A:
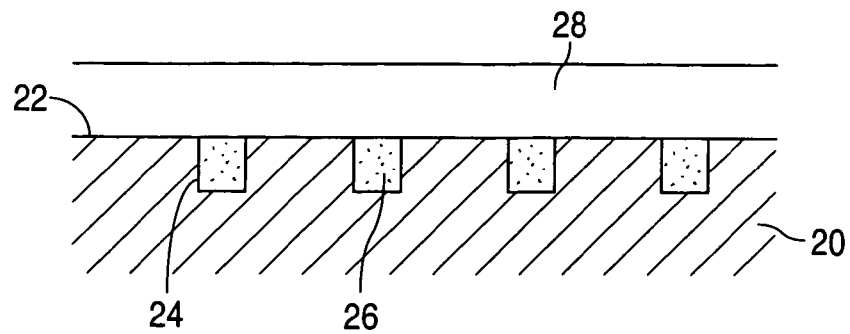
FIGS. 1A-1C illustrate coatings deposited over an implantable medical substrate in accordance with various embodiments of the present invention.

Herein is disclosed a method of forming a coating for an implantable device including applying a first composition with 40-O-(2-hydroxy)ethyl-rapamycin, or a functional analog or structural derivative thereof, to at least a portion of an implantable device to form a first layer. The release rate of 40-O-(2-hydroxy)ethyl-rapamycin is advantageously controlled by various methods and coatings as described below. In particular, by using the methods and coatings of the present invention, the amount of the 40-O-(2-hydroxy)ethyl-rapamycin, or analog or derivative thereof, is released in less than about 50% in 24 hours.

40-O-(2-hydroxy)ethyl-rapamycin is an immunosuppressant which is under investigation primarily for use with cyclosporine/steroids to prevent acute rejection episodes in renal transplant recipients. 40-O-(2-hydroxy)ethyl-rapamycin is also under investigation for rejection prophylaxis following other types of transplantation (e.g., lung, liver). The chemical structure for 40-O-(2-hydroxy)ethyl-rapamycin is as follows:

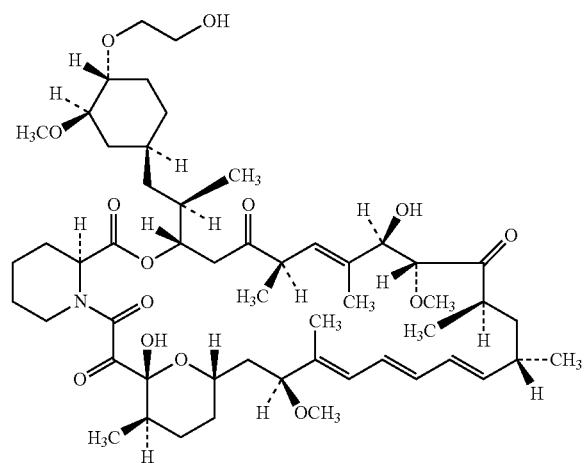

Examples of analogs or derivatives of 40-O-(2-hydroxy) ethyl-rapamycin include but are not limited to 40-O-(2-hydroxy)propyl-rapamycin and 40-O-(2-hydroxy)ethoxy] ethyl-rapamycin.

40-O-(2-hydroxy)ethyl-rapamycin binds to the cytosolic immunophyllin FKBP12 and inhibits growth factor-driven cell proliferation, including that of T-cells and vascular smooth muscle cells. The actions of 40-O-(2-hydroxy)ethyl-rapamycin occur late in the cell cycle (i.e., late G1 stage) compared to other immunosuppressive agents such as tacrolimus or cyclosporine which block transcriptional activation of early T-cell-specific genes. Since 40-O-(2-hydroxy)ethyl-rapamycin can act as a potent anti-proliferative agent, it is believed that 40-O-(2-hydroxy)ethyl-rapamycin can be an effective agent to treat restenosis by being delivered to a local treatment site from a polymeric coated implantable device such as a stent.

The composition including 40-O-(2-hydroxy)ethyl-rapamycin can be applied to the implantable device in various ways. In one embodiment, a first layer can be formed on the implantable device by (1) immersing the implantable device into a solution containing 40-O-(2-hydroxy)ethyl-rapamycin dissolved in a suitable solvent, or (2) spray coating the implantable device with the same solution containing 40-O-(2-hydroxy)ethyl-rapamycin to form a reservoir layer. In this embodiment, the implantable device can include cavities or micro-pores for containing the 40-O-(2-hydroxy)ethyl-rapamycin.

The 40-O-(2-hydroxy)ethyl-rapamycin can also be blended with a polymer and applied to the implantable device to form the reservoir layer. "Polymer," "poly," and "polymeric" are defined as compounds that are the product of a polymerization reaction and are inclusive of homopolymers, copolymers, terpolymers etc., including random, alternating, block, and graft variations thereof. The polymers should have a high capacity of adherence to the surface of an implantable device, such as a metallic surface of a stent, and a high capacity of adherence to polymeric surfaces.

In accordance with one embodiment, when the 40-O-(2-hydroxy)ethyl-rapamycin is blended with a polymer for the reservoir layer, the ratio of 40-O-(2-hydroxy)ethyl-rapamycin, or analog or derivative thereof, to polymer by weight in the reservoir layer is about 1:2.8 to about 1:1. It has been found that this particular range of 40-O-(2-hydroxy)ethyl-rapamycin:polymer ratio provides a beneficial release rate of the 40-O-(2-hydroxy)ethyl-rapamycin from the polymer matrix.

In accordance with another embodiment, when the 40-O-(2-hydroxy)ethyl-rapamycin is blended with a polymer for the reservoir layer, the 40-O-(2-hydroxy)ethyl-rapamycin, or analog or derivative thereof, is in the amount of about 50 μg to about 500 μg, more narrowly about 90 μg to about 350 μg, and the polymer is in the amount of about 50 μg to about 1000 μg, more narrowly about 90 μg to about 500 μg. These particular ranges of amounts for 40-O-(2-hydroxy)ethyl-rapamycin and a polymer can provide a beneficial release rate of the 40-O-(2-hydroxy)ethyl-rapamycin from the polymer matrix.

When the polymer solution is being prepared, a predetermined amount of a polymer can be added to a predetermined amount of a compatible solvent. "Solvent" is defined as a liquid substance or composition that is compatible with the components of the composition and is capable of dissolving the component(s) at the concentration desired in the composition. Representative examples of solvents include chloroform, acetone, water (buffered saline), dimethylsulfoxide (DMSO), propylene glycol methyl ether (PM,) iso-propylalcohol (IPA), n-propylalcohol, methanol, ethanol, tetrahydrofuran (THF), dimethylformamide (DMF), dimethylacetamide (DMAC), benzene, toluene, xylene, hexane, cyclohexane, pentane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, formamide, hexafluoroisopropanol, 1,1,1-trifluoroethanol, and hexamethyl phosphoramide and a combination thereof.

The polymer can be added to the solvent at ambient pressure and under anhydrous atmosphere. If necessary, gentle heating and stirring and/or mixing can be employed to effect dissolution of the polymer into the solvent, for example 12 hours in a water bath at about 60° C.

Sufficient amounts of 40-O-(2-hydroxy)ethyl-rapamycin can then be dispersed in the blended composition of the polymer and the solvent. The polymer can comprise from about 0.1% to about 35%, more narrowly from about 0.5% to about 20% by weight of the total weight of the composition, the solvent can comprise from about 59.9% to about 99.8%, more narrowly from about 79% to about 99% by weight of the total weight of the composition, and the 40-O-(2-hydroxy)ethyl-rapamycin can comprise from about 0.1% to about 40%, more narrowly from about 1% to about 9% by weight of the total weight of the composition. More than 9% by weight of the 40-O-(2-hydroxy)ethyl-rapamycin could adversely affect characteristics that are desirable in the polymeric coating, such as adhesion of the coating to the device. With the use of the optional primer layer, weight ratios of more than 9% for the active ingredient are achievable without compromising the effectiveness of the adhesion. Selection of a specific weight ratio of the polymer and solvent is dependent on factors such as, but not limited to, the material from which the device is made, the geometrical structure of the device, and the type and amount of the active ingredient employed.

Optionally, a second solvent, such as tetrahydrofuran (THF) or dimethylformamide (DMF), can be used to improve the solubility of the 40-O-(2-hydroxy)ethyl-rapamycin in the composition. The second solvent can be added to the composition or the 40-O-(2-hydroxy)ethyl-rapamycin can be added to the second solvent prior to mixture with the blend.

The 40-O-(2-hydroxy)ethyl-rapamycin should be in true solution or saturated in the blended composition. If the 40-O-(2-hydroxy)ethyl-rapamycin is not completely soluble in the composition, operations including mixing, stirring, and/or agitation can be employed to effect homogeneity of the residues. The 40-O-(2-hydroxy)ethyl-rapamycin can also be first added to the second solvent prior to admixing with the composition. The 40-O-(2-hydroxy)ethyl-rapamycin may be added so that the dispersion is in fine particles.

Representative examples of polymers that can be combined with 40-O-(2-hydroxy)ethyl-rapamycin for the reservoir layer include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose acetate; cellulose butyrate; cellulose acetate butyrate; cellophane; cellulose nitrate; cellulose propionate; cellulose ethers; and carboxymethyl cellulose.

Ethylene vinyl alcohol is functionally a very suitable choice of polymer. Ethylene vinyl alcohol copolymer refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. Ethylene vinyl alcohol copolymers are available commercially from companies such as Aldrich Chemical Company, Milwaukee, Wis., or EVAL Company of America, Lisle, Ill., or can be prepared by conventional polymerization procedures that are well known to one of ordinary skill in the art.

The copolymer of EVAL allows for good control capabilities of the release rate of the 40-O-(2-hydroxy)ethyl-rapamycin. As a general rule, an increase in the amount of the ethylene comonomer content decreases the rate that the 40-O-(2-hydroxy)ethyl-rapamycin is released from the copolymer matrix. The release rate of the 40-O-(2-hydroxy)ethyl-rapamycin typically decreases as the hydrophilicity of the copolymer decreases. An increase in the amount of the ethylene comonomer content increases the overall hydrophobicity of the copolymer, especially as the content of vinyl alcohol is concomitantly reduced. It is also thought that the release rate and the cumulative amount of the active ingredient that is released is directly proportional to the total initial content of the ingredient in the copolymer matrix. Accordingly, a wide spectrum of release rates can be achieved by modifying the ethylene comonomer content and the initial amount of the 40-O-(2-hydroxy)ethyl-rapamycin.

Besides 40-O-(2-hydroxy)ethyl-rapamycin, another active agent can also be added to the first composition. The additional active agent may be any substance capable of exerting a therapeutic or prophylactic effect in the practice of the present invention. Examples of such active agents include antiproliferative, antineoplastic, antiinflammatory, antiplatelet, anticoagulant, antifibrin, antithrombin, antimitotic, antibiotic, and antioxidant substances as well as combinations thereof. A suitable example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Examples of suitable antineoplastics include paclitaxel and docetaxel. Examples of suitable antiplatelets, anticoagulants, antifibrins, and antithrombins include aspirin, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocor). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as captopril (available from Squibb), cilazapril (available from Hoffman-LaRoche), or lisinopril (available from Merck & Co., Whitehouse Station, N.J.); calcium channel blockers (such as nifedipine), colchicine, fibroblast growth factor (FGF) antagonists, histamine antagonist, lovastatin (an inhibitor of HMG-CoA reductase, a cholesterol lowering drug from Merck &Co.), monoclonal antibodies (such as PDGF receptors), nitroprusside, phosphodiesterase inhibitors, prostaglandin inhibitor (available form Glaxo), suramin (a PDGF antagonist), serotonin blockers, thioprotease inhibitors, triazolopyrimidine (a PDGF antagonist), and nitric oxide. Other therapeutic substances or agents that may be appropriate include alpha-interferon; genetically engineered epithelial cells; dexamethasone; rapamycin; estradiol; clobetasol propionate; cisplatin; insulin sensitizers; receptor tyrosine kinase inhibitors; and carboplatin. Exposure of the composition to the active ingredient should not adversely alter the active ingredient's composition or characteristic. Accordingly, the particular active ingredient is selected for compatibility with the blended composition.

The dosage or concentration of 40-O-(2-hydroxy)ethyl-rapamycin or other active agent required to produce a therapeutic effect should be less than the level at which the 40-O-(2-hydroxy)ethyl-rapamycin or other active agent produces unwanted toxic effects and greater than the level at which non-therapeutic results are obtained. The dosage or concentration of 40-O-(2-hydroxy)ethyl-rapamycin or other active agent required to inhibit the desired cellular activity of the vascular region, for example, can depend upon factors such as the particular circumstances of the patient; the nature of the trauma; the nature of the therapy desired; the time over which the ingredient administered resides at the vascular site; and if other bioactive substances are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Forming a Barrier Layer to Reduce the Rate of Release

In some coatings, the release rate of the 40-O-(2-hydroxy)ethyl-rapamycin may be too high to be clinically useful. For example, in Example 22 below, the percentage of 40-O-(2-hydroxy)ethyl-rapamycin released from a stent coating without a barrier layer in 24 hours was determined to be 58.55 as measured in a porcine serum release rate procedure. The release rate from the coating of Example 22 may be too high for a treatment using 40-O-(2-hydroxy)ethyl-rapamycin as the active agent. The barrier layer of the present invention can reduce the rate of release or delay the time at which the 40-O-(2-hydroxy)ethyl-rapamycin is released from the reservoir layer.

In accordance with one embodiment, the barrier layer can be applied on a selected region of the reservoir layer to form a rate reducing member. The composition for the barrier layer can be substantially free of active agents. Alternatively, for maximum blood compatibility, compounds such as polyethylene glycol, heparin, heparin derivatives having hydrophobic counterions, or polyethylene oxide can be added to the barrier layer.

The choice of polymer for the barrier layer can be the same as the selected polymer for the reservoir. The use of the same polymer, as described for some of the embodiments, significantly reduces or eliminates any interfacial incompatibilities, such as lack of adhesion, which may exist in the employment of two different polymeric layers.

Representative examples of polymers that can be used for a barrier layer can include polytetrafluoroethylene, perfluoro elastomers, ethylene-tetrafluoroethylene copolymer, fluoroethylene-alkyl vinyl ether copolymer, polyhexafluoropropylene, low density linear polyethylenes having high molecular weights, ethylene-olefin copolymers, atactic polypropylene, polyisobutene, polybutylenes, polybutenes, styrene-ethylene-styrene block copolymers, styrene-butylene-styrene block copolymers, styrene-butadiene-styrene block copolymers, and ethylene methacrylic acid copolymers of low methacrylic acid content.

Ethylene vinyl alcohol is functionally a very suitable choice of polymer. The copolymer allows for good control capabilities over the release rate of the 40-O-(2-hydroxy) ethyl-rapamycin. As a general rule, an increase in the amount of the ethylene comonomer content decreases the rate that the 40-O-(2-hydroxy)ethyl-rapamycin is released from the copolymer matrix. The release rate of the 40-O-(2-hydroxy) ethyl-rapamycin decreases as the hydrophilicity of the polymer decreases. An increase in the amount of the ethylene comonomer content increases the overall hydrophobicity of the copolymer, especially as the content of vinyl alcohol is concomitantly reduced.

Fluoropolymers are also a suitable choice for the barrier layer composition. For example, polyvinylidene fluoride (otherwise known as KYNAR, available from ATOFINA Chemicals, Philadelphia, Pa.) can be dissolved in HFE FLUX REMOVER (Techspray, Amarillo, Tex.) and can optionally be combined with EVAL to form the barrier layer composition. Also, solution processing of fluoropolymers is possible, particularly the low crystallinity varieties such as CYTOP available from Asahi Glass and TEFLON AF available from DuPont. Solutions of up to about 15% (wt/wt) are possible in perfluoro solvents, such as FC-75 (available from 3M under the brand name FLUORINERT), which are non-polar, low boiling solvents. Such volatility allows the solvent to be easily and quickly evaporated following the application of the polymer-solvent solution to the implantable device.

In one embodiment, polybutylmethacrylate can be used for the barrier layer. Polybutylmethacrylate, for example, can be dissolved in a solution of xylene, acetone and HFE FLUX REMOVER.

The barrier layer can also be styrene-ethylene/butylene-styrene block copolymer. Styrene-ethylene/butylene-styrene block copolymer, e.g., Kraton G-series, can be dissolved in non-polar solvents such as, but not limited to, toluene, xylene, and decalin.

Other choices of polymers for the rate-limiting membrane include, but are not limited to, ethylene-anhydride copolymers; ethylene vinyl acetate copolymers having, for example, a mol % of vinyl acetate of from about 9% to about 25%; and ethylene-acrylic acid copolymers having, for example, a mol % of acrylic acid of from about 2% to about 25%. The ethylene-anhydride copolymer available from Bynel adheres well to EVAL and thus would function well as a barrier layer over a reservoir layer made from EVAL. The copolymer can be dissolved in organic solvents, such as dimethylsulfoxide and dimethylacetamide. Ethylene vinyl acetate polymers can be dissolved in organic solvents, such as toluene and n-butyl acetate. Ethylene-acrylic acid copolymers can be dissolved in organic solvents, such as methanol, isopropyl alcohol, and dimethylsulfoxide.

Yet another choice of polymer for the rate-limiting membrane is a cross-linked silicone elastomer. Loose silicone and silicone with very low cross-linking are thought to cause an inflammatory biological response. However, it is believed that a thoroughly cross-linked silicone elastomer, having low levels of leachable silicone polymer and oligomer, is an essentially non-inflammatory substance. Silicone elastomers, such as Nusil MED-4750, MED-4755, or MED2-6640, having high tensile strengths, for example between 1200 psi and 1500 psi, will likely have the best durability during crimping, delivery, and expansion of a stent as well as good adhesion to a reservoir layer, e.g., EVAL or the surface of an implantable device.

The embodiments of the composition for a rate-reducing membrane or diffusion barrier layer are prepared by methods wherein all components are combined, then blended. More particularly, a predetermined amount of a polymer can be added to a predetermined amount of a compatible solvent. The selected solvent should be capable of placing the polymer into solution at the concentration desired.

The polymer can be added to the solvent at ambient pressure and under anhydrous atmosphere. If necessary, gentle heating and stirring and/or mixing can be employed to effect dissolution of the polymer into the solvent, for example 12 hours in a water bath at about 60° C. The polymer can comprise from about 0.1% to about 35%, more narrowly from about 1% to about 20% by weight of the total weight of the composition, and the solvent can comprise from about 65% to about 99.9%, more narrowly from about 80% to about 98% by weight of the total weight of the composition. Selection of a specific weight ratio of the polymer and solvent is dependent on factors such as, but not limited to, the type of polymer and solvent employed, the type of underlying reservoir layer, and the method of application.

In an embodiment, the barrier layer contains a polymer in the amount of about 25 µg to about 500 µg, more narrowly about 65 µg to about 350 µg. This particular range for the amount of barrier polymer can provide a beneficial release rate of the 40-O-(2-hydroxy)ethyl-rapamycin from the polymer matrix.

Forming a Primer Layer

The presence of an active ingredient in a polymeric matrix can interfere with the ability of the matrix to adhere effectively to the surface of the device. Increasing the quantity of the active ingredient reduces the effectiveness of the adhesion. High drug loadings in the coating can hinder the retention of the coating on the surface of the device. A primer layer can serve as a functionally useful intermediary layer between the surface of the device and an active ingredient-containing or reservoir coating. The primer layer provides an adhesive tie between the reservoir coating and the device—which, in effect, would also allow for the quantity of the active ingredient in the reservoir coating to be increased without compromising the ability of the reservoir coating to be effectively contained on the device during delivery and, if applicable, expansion of the device.

The composition for a primer layer is prepared by conventional methods wherein all components are combined, then blended. More particularly, a predetermined amount of a polymer or a prepolymer can be added to a predetermined amount of a solvent or a combination of solvents. The mixture can be prepared at ambient pressure and under anhydrous atmosphere. Heating and stirring and/or mixing can be employed to effect dissolution of the polymer into the solvent.

Representative examples of suitable polymers for the primer layer include, but are not limited to, polyisocyanates, such as triisocyanurate and polyurethanes with polyisocyanate and/or polyisocyanate moieties based on diphenylmethane diisocyanate; acrylates, such as copolymers of ethyl acrylate and methacrylic acid; titanates, such as tetra-isopropyl titanate and tetra-n-butyl titanate; zirconates, such as n-propyl zirconate and n-butyl zirconate; silane coupling agents, such as 3-aminopropyltriethoxysilane and (3-glydidoxypropyl) methyldiethoxysilane; high amine content polymers, such as polyethyleneamine, polyallylamine, and polylysine; polymers with a high content of hydrogen bonding groups, such as polyethylene-co-polyvinyl alcohol, ethylene vinyl acetate, and melamine formaldehydes; and unsaturated polymers and prepolymers, such as polycaprolactone diacrylates, polyacrylates with at least two acrylate groups, and polyacrylated polyurethanes. With the use of unsaturated prepolymers, a free radical or UV initiator can be added to the composition for the thermal or UV curing or cross-linking process, as is understood by one of ordinary skill in the art.

Representative examples of polymers that can be used for the primer material also include those polymers that can be used for the reservoir layer as described above. The use of the same polymer significantly reduces or eliminates any interfacial incompatibilities, such as lack of an adhesive tie or bond, which may exist with the employment of two different polymeric layers.

Ethylene vinyl alcohol is a very suitable choice of polymer for the primer layer. The copolymer possesses good adhesive qualities to the surface of a stent, particularly stainless steel surfaces, and has illustrated the ability to expand with a stent without any significant detachment of the copolymer from the surface of the stent. The copolymer can comprise a mole percent of ethylene of from about 27% to about 48%.

By way of example, and not limitation, the polymer can comprise from about 0.1% to about 35%, more narrowly from about 1% to about 20% by weight of the total weight of the composition, and the solvent can comprise from about 65% to about 99.9%, more narrowly from about 80% to about 98% by weight of the total weight of the primer composition. A specific weight ratio is dependent on factors such as the material from which the implantable device is made, the geometrical structure of the device, the choice of polymer-solvent combination, and the method of application.

In accordance with another embodiment, a fluid can be added to the composition to enhance the wetting of the primer composition for a more uniform coating application. To enhance the wetting of the composition, a suitable fluid typically has a high capillary permeation. Capillary permeation or wetting is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle indicates a higher wetting liquid. A suitably high capillary permeation corresponds to a contact angle less than about 90°. The wetting fluid, typically, should have a viscosity not greater than about 50 centipoise, narrowly about 0.3 to about 5 centipoise, more narrowly about 0.4 to about 2.5 centipoise. The wetting fluid, accordingly, when added to the composition, reduces the viscosity of composition.

The wetting fluid should be compatible with the polymer and the solvent and should not precipitate the polymer. The wetting fluid can also act as the solvent. Useful examples of the wetting fluid include, but are not limited to, tetrahydrofuran (THF), dimethylformamide (DMF), 1-butanol, n-butyl acetate, dimethyl acetamide (DMAC), and mixtures and combinations thereof.

Forming a Finishing Layer

Depending on the polymer used for the reservoir or barrier layers, it may be advantageous to form a finishing layer that is especially biocompatible on the surface of the coating that is exposed to the biological lumen when inserted into a patient. Representative examples of suitable biocompatible polymers or biocompatible agents for the finishing layer include, but are not limited to ethylene vinyl alcohol copolymer, polyethylene oxide, polyethylene glycol, hyaluronic acid, polyvinyl pyrrolidone, heparin, heparin derivatives such as those having hydrophobic counterions, and phosphylcholine.

Methods for Applying the Compositions to the Device

Application of the composition can be by any conventional method, such as by spraying the composition onto the prosthesis or by immersing the prosthesis in the composition. Operations such as wiping, centrifugation, blowing, or other web-clearing acts can also be performed to achieve a more uniform coating. Briefly, wiping refers to physical removal of excess coating from the surface of the stent; centrifugation refers to rapid rotation of the stent about an axis of rotation; and blowing refers to application of air at a selected pressure to the deposited coating. Any excess coating can also be vacuumed off the surface of the device. The addition of a wetting fluid leads to a consistent application of the composition which also causes the coating to be uniformly deposited on the surface of the prosthesis.

With the use of the thermoplastic polymers for the primer, such as ethylene vinyl alcohol copolymer, polycaprolactone, poly(lactide-co-glycolide), poly(hydroxybutyrate), etc., the deposited primer composition should be exposed to a heat treatment at a temperature in a range greater than about the glass transition temperature ($T_g$) and less than about the melting temperature ($T_m$) of the selected polymer. Unexpected results have been discovered with treatment of the composition under this temperature range, specifically strong adhesion or bonding of the coating to the metallic surface of a stent. The device should be exposed to the heat treatment for any suitable duration of time that would allow for the formation of the primer coating on the surface of the device as well as for the evaporation of the solvent or combination of solvent and wetting fluid. It is understood that essentially all of the solvent and the wetting fluid will be removed from the composition, but traces or residues may remain blended with the polymer.

Table 1 lists the $T_g$ and $T_m$ for some of the polymers used in the embodiments of the present invention. $T_g$ and $T_m$ of polymers are attainable by one of ordinary skill in the art. The cited exemplary temperature and time for exposure are provided by way of illustration and are not meant to be limiting.

TABLE 1

| Polymer | $T_g$ (° C.) | $T_m$ (° C.) | Exemplary Temperature (° C.) | Exemplary Duration of Time For Heating |
|---|---|---|---|---|
| EVAL | 55 | 165 | 140 | 4 hours |
| polycaprolactone | −60 | 60 | 50 | 2 hours |
| ethylene vinyl acetate (e.g., 33% vinyl acetate content) | 36 | 63 | 45 | 2 hours |
| Polyvinyl alcohol | 75-85* | 200-220* | 165 | 2 hours |

*Exact temperature depends on the degree of hydrolysis which is also known as the amount of residual acetate.

With the use of one of the aforementioned thermoset primer polymers, the use of initiators may be required. By way of example, epoxy systems consisting of diglycidyl ether of bisphenol A resins can be cured with amine curatives, thermoset polyurethane prepolymers can cured with polyols, polyamines, or water (moisture), and acrylated urethane can be cured with UV light. If baked, the temperature can be above the $T_g$ of the selected polymer.

With the use of the inorganic primer polymers, such as silanes, titanates, and zirconates, the solvent is allowed to evaporate.

The composition containing the active ingredient can be applied to a designated region of the primer coating or the surface of the device. The solvent(s) or the combination of solvent(s) and the wetting fluid is removed from the composition by allowing the solvent(s) or combination of the solvent(s) and the wetting fluid to evaporate. The evaporation can be induced by heating the device at a predetermined temperature for a predetermined period of time. For example, the device can be heated at a temperature of about 60° C. for about 12 hours to about 24 hours. The heating can be conducted in an anhydrous atmosphere and at ambient pressure and should not exceed the temperature which would adversely affect the active ingredient. The heating can also be conducted under a vacuum condition. It is understood that essentially all of the solvent and the wetting fluid will be removed from the composition, but traces or residues may remain blended with the polymer.

The diffusion barrier layer can be formed on a designated region of the active ingredient-containing coating subsequent to the evaporation of the solvent(s) or solvent(s)/wetting fluid and the drying of the polymer for the active ingredient-containing coating. Alternatively, in embodiments in which a polymeric reservoir coating is not employed, the rate-reducing membrane may be formed directly over active-ingredient containing cavities within the surface of the prosthesis. The diffusion barrier layer can be applied by spraying the composition onto the device or immersing the device in the composition, then drying the polymer. The above-described processes can be similarly repeated for the formation of the diffusion barrier layer.

Thermal Treatment of the Coating

After the coating has been formed on the implantable device, depending on the polymers used in the coating, the 40-O-(2-hydroxy)ethyl-rapamycin can diffuse from the polymer matrix at a rate that could be too high for certain clinical conditions. Accordingly, the coating can be exposed to a temperature that is effective to decrease the diffusion rate of the 40-O-(2-hydroxy)ethyl-rapamycin from the polymer matrix. In particular, the coating can be exposed to a sufficient temperature effective to decrease the release rate of the 40-O-

(2-hydroxy)ethyl-rapamycin, or analog or derivative thereof, by about 50% as compared to a control group, as demonstrated in Example 17 below.

Typically, the temperature will be between the glass transition temperature ($T_g$) and the melting temperature ($T_m$) of the polymer. For example, the temperature can be the annealing temperature of the polymer (about equal to $T_g+T_m/2$). The thermal treatment can be conducted in an anhydrous atmosphere and at ambient pressure. The treatment can also be conducted under a vacuum condition.

The exposure temperature should not adversely affect the characteristics of the 40-O-(2-hydroxy)ethyl-rapamycin or other active agents present in the coating. In order to prevent possible degradation of the active agents or the polymers in the coating, additives can be mixed with the polymer before or during the coating process to shift the thermal profile of the polymer (i.e., decrease the $T_g$ and $T_m$ of the polymer). For example, a plasticizer, which is usually a low molecular weight nonvolatile molecule, can be dissolved with the polymer before the application process. The plasticizer can be an active agent. A representative example of an additive is dioctyl phthalate.

In one embodiment, one of the polymers in the coating exposed to the temperature is a semi-crystalline (e.g., polyvinyl chloride and EVAL) polymer. Without being bound by any particular theory, it is believed that the diffusion rate of the active agent from the polymer is decreased because the thermal radiation increases the percent crystallinity of the polymer. Others types of energy, such as RF energy, can also be used to increase the percent crystallinity. "Percent crystallinity" refers to the percentage of the polymer material that is in a crystalline form. Those of ordinary skill in the art understand that there are several methods for determining the percent crystallinity in polymers. These methods are, for example, described in L. H. Sperline, Introduction to Physical Polymer Science (3rd ed. 2001). The first involves the determination of the heat of fusion of the whole sample by calorimetric methods. The heat of fusion per mole of crystalline material can be estimated independently by melting point depression experiments.

A second method involves the determination of the density of the crystalline portion via X-ray analysis of the crystal structure, and determining the theoretical density of a 100% crystalline material. The density of the amorphous material can be determined from an extrapolation of the density from the melt to the temperature of interest. Then the percent crystallinity is given by:

$$\% \ Crystallinity = \frac{\rho_{exptl} - \rho_{amorph}}{\rho_{100\% \ cryst} - \rho_{amorph}} \times 100$$

where $\rho_{exptl}$ represents the experimental density, and $\rho_{amorph}$ and $\rho_{100\% \ cryst}$ are the densities of the amorphous and crystalline portions, respectively.

A third method stems from the fact that X-ray diffraction depends on the number of electrons involved and is thus proportional to the density. Besides Bragg diffraction lines for the crystalline portion, there is an amorphous halo caused by the amorphous portion of the polymer. The amorphous halo occurs at a slightly smaller angle than the corresponding crystalline peak, because the atomic spacings are larger. The amorphous halo is broader than the corresponding crystalline peak, because of the molecular disorder. This third method can be quantified by the crystallinity index, CI, where $$CI = \frac{A_c}{A_a + A_c}$$

where $A_c$ and $A_a$ represent the area under the Bragg diffraction line and corresponding amorphous halo, respectively.

The heat emitter used to thermal treat the coating can be any apparatus that emits thermal radiation. For example, the heat emitter can be a cauterizer tip. The heat emitter can also be a blower that includes a heating device so that the blower can direct a warm gas (e.g., air, argon or nitrogen) onto the implantable device. The heating device can be any heating device as known by those of ordinary skill in the art. For example, the heating device can be an electric heater incorporating heating coils.

In one embodiment of the present invention, the thermal radiation from the heat emitter can be directed to only certain portions of the implantable device or only for certain durations so that the diffusion rates of the 40-O-(2-hydroxy)ethyl-rapamycin from the polymer differs in various portions of the coating. In one example, the implantable device can have two or more segments along the longitudinal axis of the implantable device, such as a first segment, a second segment and a third segment. The thermal radiation could be directed substantially only at the first segment and the third segment, for instance, by using a cauterizer tip. Alternatively, the thermal radiation could be set higher for the first and third segments, or the thermal radiation could be directed at the first and third segments for a longer duration than the second segment. As a result, the polymer along the first segment and the third segment would have a greater percent crystallinity than the polymer along the second segment. Therefore, the diffusion rates of the active agent from the polymer matrix along the first segment and the third segment would be less than the diffusion rate along the second segment.

In another embodiment, by limiting the time that the coating is exposed to thermal radiation so that the percent crystallinity is not maximized throughout the entire thickness of the coating, the shallower regions of the coating will have a higher percent crystallinity than the deeper regions. In a particular example, if the coating has four regions with the fourth region as the deepest, by limiting the thermal treatment, the first or shallowest region would have a higher percent crystallinity than the fourth or deepest region. One of ordinary skill in the art will understand that the duration and temperature of the exposure will depend on the desired diffusion rate of the polymer, and the inherent characteristics of the polymers used in the coating.

Sterilization of the Implantable Device

After the implantable device has been coated according to the various embodiments of the present invention, the implantable device can be sterilized by various methods. According to conventional thought, a coating containing 40-O-(2-hydroxy)ethyl-rapamycin cannot be sterilized with many techniques because the 40-O-(2-hydroxy)ethyl-rapamycin is degraded by the processes. For example, it was thought that a polymer coating containing 40-O-(2-hydroxy)ethyl-rapamycin could not be sterilized with an e-beam procedure because the free radicals produced during the process would degrade the 40-O-(2-hydroxy)ethyl-rapamycin. Similarly, it has been thought that exposing a coating with 40-O-(2-hydroxy)ethyl-rapamycin to ethylene oxide or peroxide gas would also degrade the 40-O-(2-hydroxy)ethyl-rapamycin. However, it has unexpectedly been found that the coatings of the present invention protect the 40-O-(2-hydroxy)ethyl-rapamycin during sterilization procedures (e.g., using an e-beam or ethylene oxide process). In fact, subsequent to sterilization, the peak purity of the 40-O-(2-hydroxy)ethyl-rapamycin has been greater than 90% when included in the coatings of the present invention.

In an embodiment of the present invention, the particular procedure used to sterilize the coating can also be used to expose the coating to a temperature that is effective to decrease the diffusion rate of the 40-O-(2-hydroxy)ethyl-rapamycin from the polymer matrix. In particular, during the sterilization procedure (e.g., the ethylene oxide procedure) the coating can be exposed to a sufficient temperature effective to decrease the release rate of the 40-O-(2-hydroxy)ethyl-rapamycin, or analog or derivative thereof, by about 50% as compared to a control group.

Examples of the Device

The device or prosthesis coated in accordance with embodiments of the present invention may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, 10% molybdenum. Devices made from bioabsorbable or biostable polymers could also be used with the embodiments of the present invention.

The embodiments of the present invention may be particularly useful for the coatings of small vessel stents. Small vessels stents can be generally categorized as having inner diameters of less than 2.5 mm in an expanded state. Because of their small size, small vessel stents offer unique challenges for drug delivery. In particular, as compared to conventionally sized stents, small vessel stents have a greater surface:volume ratio. Therefore, when a small vessel stent is inserted into a biological lumen, the vessel tissue surrounding a small vessel stent is exposed to a greater concentration of polymer and active agent.

The various embodiments of the present invention can be used to address some of the challenges offered by the use of small vessel stents. For example, it is thought that it is especially important that small vessel stents have lower amounts of polymer in their coatings, as compared to larger sized stents, in order to reduce the risk of an inflammatory response by the vessel tissue. However, it may also be important to have a barrier layer on the stent coating in order to have a low release rate of the active agents, such as 40-O-(2-hydroxy)ethyl-rapamycin. With the inclusion of the barrier layer, the amount of polymer on the coating may be sufficient to cause an unwanted inflammatory response. In order to address these countervailing concerns, one approach would be to provide a thinner barrier layer on the polymer matrix as compared to larger sized stents, and then heat treat the barrier layer to increase the crystallinity of the barrier layer polymer, thereby decreasing the release rate of the active agent from the reservoir region. In an alternative embodiment, the polymer used for the barrier layer can initially have a very high percent crystallinity. In yet another embodiment, the reservoir layer can be heat treated to reduce the release rate of active agent from the reservoir region without the use of a barrier layer.

In another particular example, it is thought that it is especially important for small vessel stents to have a biocompatible coating. One approach to address this need is to provide a finishing layer on the stent that contains a highly biocompatible polymer such as polyethylene glycol, or biocompatible agents such as heparin. For example, a finishing layer can be applied over a barrier layer so that the coating offers a usefully low release rate of an active agent and also provides a highly biocompatible coating.

Coating

Figure 1B:
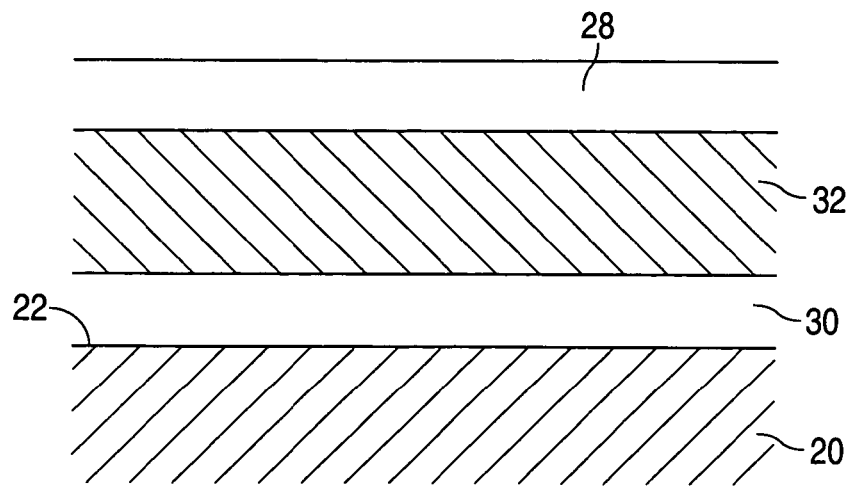
Figure 1C:
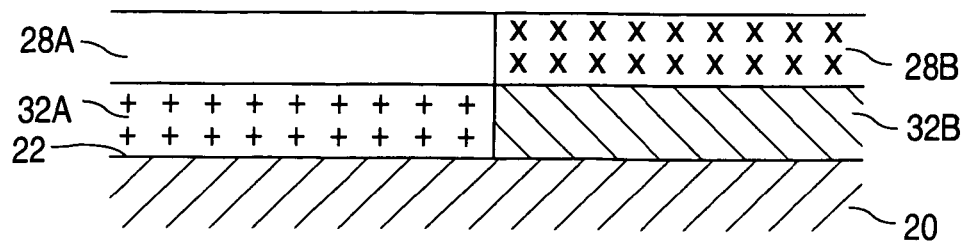

Some of the various embodiments of the present invention are illustrated by FIGS. 1A, 1B, and 1C. The Figures have not been drawn to scale, and the thickness of the various layers have been over or under emphasized for illustrative purposes.

Referring to FIG. 1A, a body of a medical substrate 20, such as a stent, is illustrated having a surface 22. Medical substrate 20 includes cavities or micro-pores 24 formed in the body for releasably containing an active ingredient, as illustrated by dotted region 26. A barrier layer or rate-reducing membrane 28 is disposed on surface 22 of medical substrate 20, covering cavities 24. Barrier layer 28 functions to reduce the rate of release of an active agent (e.g., 40-O-(2-hydroxy)ethyl-rapamycin) from medical substrate 20.

Referring to FIG. 1B, medical substrate 20 is illustrated having a primer layer 30 formed on surface 22. An active agent-containing or reservoir coating 32 is deposited on primer layer 30. Primer layer 30 serves as an intermediary layer for increasing the adhesion between reservoir coating 32 and surface 22. Increasing the amount of active ingredient admixed within the polymer diminishes the adhesiveness of reservoir layer 32 to surface 22. Accordingly, using an active agent-free polymer as an intermediary primer layer 30 allows for a higher active ingredient content for reservoir layer 32. Barrier layer 28 is formed over at least a selected portion of reservoir layer 32. One of ordinary skill in the art can appreciate that barrier layer 28 can be deposited only on selected areas of reservoir layer 32 so as to provide a variety of selected release parameters. Such selected patterns may become particularly useful if a combination of active agents are used, each of which requires a different release parameter.

FIG. 1C illustrates medical substrate 20 having a first reservoir layer 32A disposed on a selected portion of surface 22 of medical substrate 20. First reservoir layer 32A contains a first active agent, e.g., 40-O-(2-hydroxy)ethyl-rapamycin. A second reservoir layer 32B can also be disposed on surface 22. Second reservoir layer 32B contains a second active ingredient, e.g., taxol. First and second reservoir layers 32A and 32B are covered by first and second barrier layers 28A and 28B, respectively. In accordance with one embodiment, the polymeric material in barrier layer 28B has been exposed to thermal treatment, whereas the polymeric material in barrier layer 28A has not. As a result, the polymeric material in barrier 28B has a higher percent crystallinity than the polymeric material in barrier layer 28A. Accordingly, by producing a coating such as the one shown in FIG. 1C, a wide array of release parameters can be obtained for any selected combination of active agents.

Barrier layer 28 can have any suitable thickness, as the thickness of barrier layer 28 is dependent on parameters such as, but not limited to, the desired rate of release and the procedure for which the stent will be used. For example, barrier layer 28 can have a thickness of about 0.1 to about 10 microns, more narrowly from about 0.25 to about 5 microns.

By way of example, and not limitation, the impregnated reservoir layer 32 can have a thickness of about 0.5 microns to about 1.5 microns. The particular thickness of reservoir layer 32 is based on the type of procedure for which medical substrate 20 is employed and the amount of the active agent to be delivered. The amount of the active agent to be included on the prosthesis can be further increased by applying a plurality of reservoir layers 32 on top of one another. The optional primer layer 30 can have any suitable thickness, examples of which can be in the range of about 0.1 to about 10 microns, more narrowly about 0.1 to about 2 microns.

Method of Use

In accordance with the above-described method, the active agent can be applied to a device, e.g., a stent, retained on the device during delivery and released at a desired control rate and for a predetermined duration of time at the site of implantation. A stent having the above-described coating layers is useful for a variety of medical procedures, including, by way of example, treatment of obstructions caused by tumors in bile ducts, esophagus, trachea/bronchi and other biological passageways. A stent having the above-described coating layers is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. Angiography is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter, which allows a stent in its collapsed configuration to be inserted into the passageway. The delivery catheter is inserted either percutaneously, or by surgery, into the femoral artery, brachial artery, femoral vein, or brachial vein, and advanced into the appropriate blood vessel by steering the catheter through the vascular system under fluoroscopic guidance. A stent having the above-described coating layers may then be expanded at the desired area of treatment. A post insertion angiogram may also be utilized to confirm appropriate positioning.

EXAMPLES

The embodiments of the present invention will be illustrated by the following set forth examples.

Example 1

35 13 mm PENTA stents (available from Guidant Corporation) were coated by spraying a 2% (w/w) solution of poly (ethylene-co-vinyl alcohol) (44 mole % ethylene) ("EVAL") in 98% (w/w) dimethylacetamide. The solvent was removed by baking at 140° C. for 2 hours. A solution of 1.9% (w/w) EVAL and 0.7% (w/w) 40-O-(2-hydroxy)ethyl-rapamycin in a mixture of 68.2% (w/w) dimethylacetamide and 29.2% (w/w) ethanol was spray coated onto the stents to a thickness with a target of 175 µg of 40-O-(2-hydroxy)ethyl-rapamycin on each stent. The stents were then baked at 50° C. for 2 hours. A barrier layer was formed by spraying the stents with a 4% (w/w) solution of EVAL in a mixture of 76% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 40 µg of polymer, and a measured average dry weight of 43±3 µg of polymer. For the reservoir layer, the target drug:polymer ratio was 1:2.857, the target dry weight for the entire reservoir coating was 675 µg and the average actual dry weight was 683±19 µg. Also for the reservoir layer, the average total drug content of the stent coatings was determined by the process described in Example 2. The average drug content was 133 µg or 152 µg/cm$^2$. For the barrier layer, the target dry weight of polymer was 300 µg and the measured average dry weight was 320±13 µg.

Example 2

A drug-coated stent was placed in a volumetric flask. An appropriate amount of the extraction solvent acetonitrile with 0.02% BHT as protectant was added (e.g., in a 10 ml volumetric flask, with about 9 ml solvent added). The flask was sonicated for a sufficient time to extract all of the drug from the reservoir region. Then, the solution in the flask was filled to mark with the solvent solution. The drug solution was the analyzed by HPLC. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 µm particle size), maintained at a temperature of 40° C. The mobile phase consisted of 75% acetonitrile and 25% 20 mMolar ammonium acetate. The flow rate was set on 1 ml/min. The HPLC release rate results were quantified by comparing the results with a reference standard. The total drug content of the stent was then calculated.

Example 3

34 13 mm PENTA stents were coated by spraying a 2% (w/w) solution of EVAL and 98% (w/w) dimethylacetamide. The solvent was removed by baking at 140° C. for 2 hours. A solution of 1.9% (w/w) EVAL and 1.1% (w/w) 40-O-(2-hydroxy)ethyl-rapamycin in a mixture of 67.9% (w/w) dimethylacetamide and 29.1% (w/w) ethanol was spray coated onto the stents to a thickness with a target of 275 µg of 40-O-(2-hydroxy)ethyl-rapamycin on each stent. The stents were then baked at 50° C. for 2 hours. A barrier layer was formed by spraying the stents with a 4% (w/w) solution of EVAL in a mixture of 76% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 40 µg of polymer, and a measured average dry weight of 43±3 µg of polymer. For the reservoir layer, the target drug:polymer ratio was 1:1.75, the target dry weight for the entire reservoir coating was 757 µg and the average actual dry weight was 752±23 µg. Also for the reservoir layer, the average total drug content of the stent coatings was determined by the process described in Example 2. The average drug content was 205 µg or 235 µg/cm$^2$. For the barrier layer, the target dry weight of polymer was 200 µg and the measured average dry weight was 186±13 µg.

Example 4

24 13 mm PENTA stents were coated by spraying a 2% (w/w) solution of EVAL and 98% (w/w) dimethylacetamide.

The solvent was removed by baking at 140° C. for 2 hours. A solution of 1.9% (w/w) EVAL and 1.2% (w/w) 40-O-(2-hydroxy)ethyl-rapamycin in a mixture of 67.8% (w/w) dimethylacetamide and 29.1% (w/w) ethanol was spray coated onto the stents to a thickness with a target of 325 µg of 40-O-(2-hydroxy)ethyl-rapamycin on each stent. The stents were then baked at 50° C. for 2 hours. A barrier layer was formed by spraying the stents with a 4% (w/w) solution of EVAL in a mixture of 76% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 40 µg of polymer, and a measured average dry weight of 41±2 µg of polymer. For the reservoir layer, the target drug:polymer ratio was 1:1.6, the target dry weight for the entire reservoir coating was 845 µg and the average actual dry weight was 861±16 µg. Also for the reservoir layer, the average total drug content of the stent coatings was determined by the process described in Example 2. The average drug content was 282 µg or 323 µg/cm². For the barrier layer, the target dry weight of polymer was 125 µg and the measured average dry weight was 131±9 µg.

Example 5

This Example 5 is referred to as the "Release Rate Profile Procedure." A drug-coated stent was placed on a stent holder of a Vankel Bio-Dis release rate tester (Vankel, Inc., Cary, N.C.). The stent was dipped into an artificial medium which stabilizes the 40-O-(2-hydroxy)ethyl-rapamycin in the testing solution, including a phosphate buffer saline solution (10 mM, pH 7.4) with 1% TRITON X-100 (Sigma Corporation), for a designated amount of time (e.g., 3 hours). Then the solution was analyzed for the amount of drug released from the stent coating using an HPLC process. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 µm particle size), maintained at a temperature of 40° C. The mobile phase consisted of 75% acetonitrile and 25% 20 mMolar ammonium acetate. The flow rate was set on 1 ml/min. After the drug solution was analyzed by HPLC the results were quantified by comparing the release rate results with a reference standard.

If the experimental protocol required that the stent coating be subjected to experimental conditions for an additional time, the stent was then dipped in a fresh medium solution for the necessary amount of time (e.g., another 3 hours) and the drug released in the solution was analyzed again according to the HPLC procedure described above. The procedure was repeated according to the number of data points required. The release rate profile could then be generated by plotting cumulative drug released in the medium vs. time.

Example 6

The release rate of 40-O-(2-hydroxy)ethyl-rapamycin from the stents with coatings produced by the processes under Examples 1, 3 and 4 were tested using the in vitro HPLC process as described in Example 5. The solution for each stent underwent two HPLC runs, and the results were averaged.

The following Table 2 summarizes the results of the release rate procedure for two stents from Example 1:

TABLE 2

| | Time (hrs) | | | | | | |
|---|---|---|---|---|---|---|---|
| | 3 | 6 | 9 | 12 | 23 | 32 | 48 |
| Cumulative Release from Stent 1 (µg) | 3.72 | 5.62 | 7.12 | 8.43 | 12.28 | 15.31 | 20.28 |
| Cumulative Release from Stent 2 (µg) | 4.18 | 6.53 | 8.54 | 10.29 | 15.64 | 19.66 | 26.3 |

The following Table 3 summarizes the results of the release rate procedure for two stents from Example 3:

TABLE 3

| | Time (hrs) | | | | | | |
|---|---|---|---|---|---|---|---|
| | 3 | 6 | 9 | 12 | 23 | 32 | 48 |
| Cumulative Release from Stent 1 (µg) | 29.73 | 45.35 | 57.79 | 68.19 | 95.2 | 110.85 | 130.75 |
| Cumulative Release from Stent 2 (µg) | 26.36 | 41.2 | 53.5 | 63.99 | 93.93 | 112.31 | 135.7 |

The following Table 4 summarizes the results of the release rate procedure for two stents from Example 4:

TABLE 4

| | Time (hrs) | | | | | | |
|---|---|---|---|---|---|---|---|
| | 3 | 6 | 9 | 12 | 23 | 32 | 48 |
| Cumulative Release from Stent 1 (µg) | 46.24 | 67.4 | 82.79 | 94.92 | 124.72 | 141.96 | 165.12 |
| Cumulative Release from Stent 2 (µg) | 44.66 | 66.74 | 82.26 | 94.49 | 123.92 | 140.07 | 159.65 |

Figure 2:
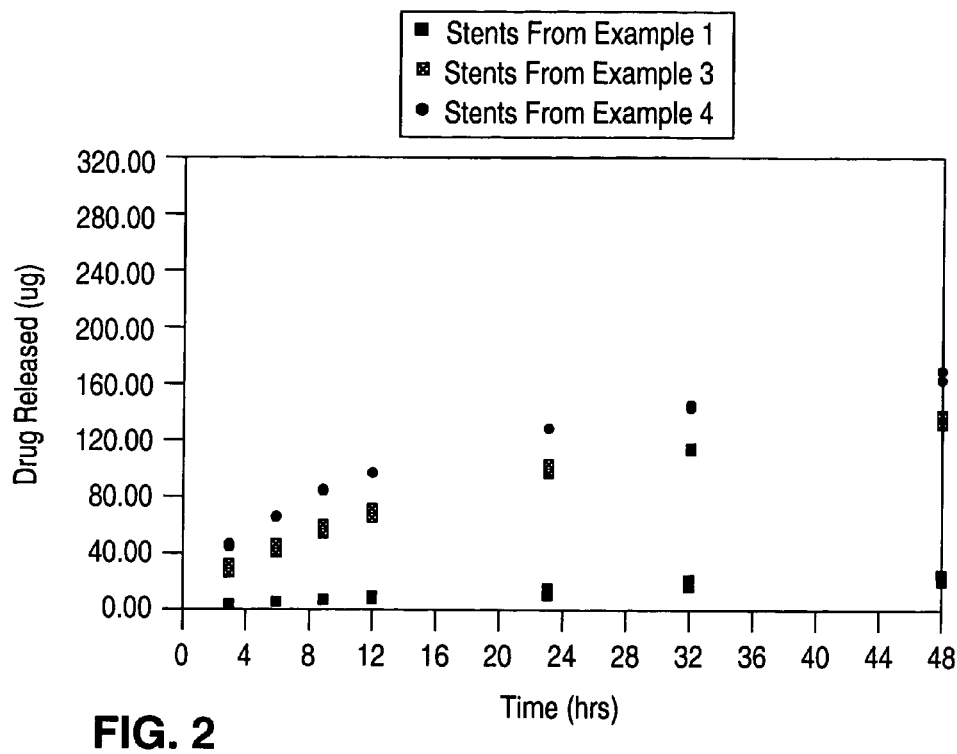
FIGS. 2-3 are graphs showing the release rate of 40-O-(2-hydroxy)ethyl-rapamycin from stent coatings in accordance with embodiments of the present invention.

A comparison of the release rates for the stents from Examples 1, 3 and 4 is graphically shown in FIG. 2.

Example 7

The following Example 7 is referred to as the "3 day In Vivo Release Rate Procedure" or the "9 day In Vivo Release Rate Procedure," depending on the number of days the stents are inserted into the experimental animal. The following are the materials used for this Example:

1. Experimental animal: One 30-45 kg Yorkshire cross pig;
2. BMW™ wires 0.014", 190 cm;
3. Guide wire 0.035", 190 cm;
4. Viking guide catheters, 7F;
5. Introducer sheaths (8-10F);
6. ACS 20/20 Indeflator™ Inflation Device;
7. Saline; solution with heparin;
8. Nitroglycerin, Lidocaine, other inotropic/chronotropic drugs;
9. Standard surgical equipment, anesthetic, and medications as necessary;
10. Respiratory and hemodynamic monitoring systems;
11. Positive pressure ventilator and associated breathing circuits;
12. ACT machine and accessories;

13. PTCA accessories;
14. Ambulatory defibrillator;
1. Fluoroscopy equipment; and
15. Non-ionic contrast agent;

The following was the procedure used for this Example:

A. Animal Preparation.
  2. Administer Aspirin (325 mg PO) once daily starting one day prior to stent implantation.
  3. Sedate the pig.
  4. Intubate the trachea via an oral approach.
  5. Deliver isoflurane (up to about 5%) to achieve and maintain an adequate plane of anesthesia.
  6. Shave the sheath introduction area free of hair and scrub the surgical site with surgical soap and/or antiseptic solution.
  7. Place a 7F introducer sheath into the right or left femoral artery.
  8. Obtain an arterial blood sample for a baseline ACT.
  9. Administer heparin 200 units/kg IV (not to exceed 100,000 units) and obtain a blood sample for measurement of ACT 5-10 minutes later.
  10. Repeat heparin as needed to maintain ACT ≧300 seconds.
  11. Measure and record arterial blood pressure, heart rate and electrocardiogram (ECG).

B. Angiography for Vessel Selection.
  1. Advance the guiding catheter over the guidewire into the aortic arch and cannulate the desired vessel.
  2. Administer nitroglycerin (200 μg) intra-luminally prior to baseline angiography.
  3. Perform baseline angiogram and record images on cine.
  4. With the diameter of the guiding catheter as a reference, select vasculature that will allow a target stent to artery ratio of about 1.1:1.0.

C. Stent Preparation and Deployment.
  1. Perform online QCA and measure baseline proximal, target, and distal reference sites.
  2. Administer nitroglycerin (200 μg) intra-luminally prior to stent deployment, then as needed to control coronary artery vasospasm.
  3. Inspect the stent delivery system. Ensure that the stent is correctly positioned on the balloon. Inspect the stent for any abnormalities.
  4. Flush guidewire lumen with heparinized saline until fluid exits the guidewire notch.
  5. Prepare Indeflator/syringe with diluted (approximately 50:50) contrast medium.
  6. Attach syringe to test catheter inflation port; use standard techniques to fill the inflation lumen with diluted contrast.
  7. Purge syringe and test catheter inflation lumen of all air.
  8. Purge Indeflator of all air and attach to test catheter inflation port.
  9. Position an appropriate guidewire in the distal bed of the target artery.
  10. Insert the stent delivery system through the guiding catheter over the guidewire.
  11. Advance the stent delivery system to the pre-selected arterial deployment site.
  12. Position balloon for inflation.
  13. Refer to IFU for inflation strategy. If no IFU available, inflate the balloon at a slow steady rate to a pressure that expands the stent to the desired diameter. Hold at this pressure for 30 seconds.
  14. Record inflated balloon by pulling image on cine. Perform on-line QCA and measure the inflated balloon diameter.
  15. Deflate balloon by pulling negative pressure. While withdrawing the system, observe tactually and fluoroscopically. Record any resistance.
  16. Administer nitroglycerin (200 μg) intra-luminally.
  17. Assess patency, deployment, and placement of stent via coronary angiography.
  18. Assess TIMI angiographic low grade.
  19. Record on cine and video.
  20. Measure post-proximal, target, and distal MLD with QCA.
  21. Repeat Section C with remaining stent delivery system.
  22. Measure and record heart rate, arterial blood pressure and electrocardiogram (ECG).

D. Stent Procedure End.
  1. Remove the guidewire, guiding catheter and introducer sheath.
  2. Remove introducer sheath from the femoral artery.
  3. Apply pressure to the femoral artery at the side of sheath entry.
  4. Allow the animal to recover from anesthesia in an individual cage.
  5. Give Buprenorphine (0.05 mg/kg) PRN as needed for pain.
  6. Administer Ticlopidine (250 mg PO) and aspirin (325 mg PO) once daily until date of follow-up angiography.

E. Study End.
  1. Euthanize the pig with an overdose of barbiturates and/or potassium chloride.
  2. Excise the heart without flushing the vessels.
  3. Harvest all stented arteries.
  4. Remove the stent from all treated arteries and place them in dark colored amber vials for subsequent drug concentration analysis.
  5. Snap freeze the arterial tissue in liquid nitrogen and store at −70° C. until subsequent analysis of tissue for drug concentrations as determined by HPLC.

The stents harvested from the experimental animals were tested using an HPLC procedure to determine how much drug remained on the stents. A drug-coated stent removed from the experimental animal was placed in a volumetric flask. An appropriate amount of the extraction solvent acetonitrile with 0.02% BHT as protectant was added (e.g., in a 10 ml volumetric flask, with about 9 ml solvent added). The flask was sonicated for a sufficient time to extract all of the drug from the reservoir region. Then, the solution in the flask was filled to mark with the solvent solution. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 μm particle size), maintained at a temperature of 40° C. The mobile phase consisted of 75% acetonitrile and 25% 20 mMolar ammonium acetate. The flow rate was set on 1 ml/min. The HPLC release rate results were quantified by comparing the results with a reference standard. The total drug released in vivo was the difference between the average drug loaded on the stents and the amount of drug remaining on the stents after the stent implantation into the experimental animal.

Example 8

The release rate of 40-O-(2-hydroxy)ethyl-rapamycin from the stents with coatings produced by the process under Example 1 were tested using a 3 day in vivo process as described in Example 7. In particular, stents from Example 1 were implanted into experimental animals and then the stents were tested by HPLC to determine how much 40-O-(2-hydroxy)ethyl-rapamycin diffused from the stent coating into the blood vessel. According to the HPLC analysis, 21.8 μg of the 40-O-(2-hydroxy)ethyl-rapamycin was released from the coating in 3 days, or 16.4% of the total drug content of the coating.

Example 9

The release rate of 40-O-(2-hydroxy)ethyl-rapamycin from the stents with coatings produced by the process under Example 3 were tested using a 3 day in vivo process as described in Example 7. In particular, stents from Example 3 were implanted into experimental animals and then the stents were tested by HPLC to determine how much 40-O-(2-hydroxy)ethyl-rapamycin diffused from the stent coating into the blood vessel. According to the HPLC analysis, 7.8 μg of the 40-O-(2-hydroxy)ethyl-rapamycin was released from the coating in 3 days, or 3.8% of the total drug content of the coating.

Example 10

The release rate of 40-O-(2-hydroxy)ethyl-rapamycin from the stents with coatings produced by the process under Example 4 were tested using a 3 day in vivo process as described in Example 7. In particular, stents from Example 4 were implanted into experimental animals and then the stents were tested by HPLC to determine how much 40-O-(2-hydroxy)ethyl-rapamycin diffused from the stent coating into the blood vessel. According to the HPLC analysis, 50.8 μg of the 40-O-(2-hydroxy)ethyl-rapamycin was released from the coating in 3 days, or 18% of the total drug content of the coating.

Example 11

The release rate of 40-O-(2-hydroxy)ethyl-rapamycin from the stents with coatings produced by the process under Example 3 were tested using a 9 day in vivo process as described in Example 7. In particular, stents from Example 3 were implanted into experimental animals and then the stents were tested by HPLC to determine how much 40-O-(2-hydroxy)ethyl-rapamycin diffused from the stent coating into the blood vessel. According to the HPLC analysis, 29.7% of the 40-O-(2-hydroxy)ethyl-rapamycin was released from the coating in 9 days.

Example 12

The release rate of 40-O-(2-hydroxy)ethyl-rapamycin from the stents with coatings produced by the process under Example 4 were tested using a 9 day in vivo process as described in Example 7. In particular, stents from Example 4 were implanted into experimental animals and then the stents were tested by HPLC to determine how much 40-O-(2-hydroxy)ethyl-rapamycin diffused from the stent coating into the blood vessel. According to the HPLC analysis, 39.4% of the 40-O-(2-hydroxy)ethyl-rapamycin was released from the coating in 9 days.

Example 13

A 13 mm PIXEL stent (available from Guidant Corporation) was coated. The stent had a yellowish-gold coating that included ethylene vinyl alcohol copolymer and actinomycin D. The ends of the stent were heated with a cauterizer tip for fifteen (15) seconds at a current setting of 2.2 Amps, which corresponded to a temperature of about 106° C. at a distance of about 0.006 inches from the stent.

After the stent was exposed to heat from the cauterizer tip, the stent was submerged in a 50% (w/w) methanol:water bath. After twenty-four (24) hours, the stent was observed to have drug present at the stent end rings as indicated by a yellowish hue. The middle section of the stent, however, was clear, indicating that the drug had been released through the polymer. This process was repeated on 40 stents yielding similar results for all the stents.

Example 14

13 mm PIXEL stents were coated. The stents had yellowish-gold coatings that included ethylene vinyl alcohol copolymer and actinomycin D. The stents were separated into three experimental groups, and the ends of the stents were heated with a cauterizer tip according to the parameters shown in Table 5 for each group. After the stents were exposed to heat from the cauterizer tip, the stent was submerged in a 50% (w/w) methanol:water bath. After twenty-four (24) hours, the stents were observed as summarized in Table 5.

TABLE 5

| Experimental Group | Current (Amps) | Exposure Time (Seconds) | Observation |
| --- | --- | --- | --- |
| 1 | 2.0 | 10 | Least gold coloration in the end sections compared to the stents from Experimental Groups 2 and 3, indicating the least amount of drug remaining in the stent coating. |
| 2 | 2.2 | 8 | Moderate gold coloration in the end sections. |
| 3 | 2.4 | 5 | Most gold coloration in the end sections compared to the stents from Experimental Groups 1 and 2 indicating the most amount of drug remaining in the stent coating. |

It was observed that the coating in the middle section of the stents, which did not have significant exposure to heat from the cauterizer tip, was clear. This indicates that the drug had been eluted from the stents. On the other hand, the end rings of the stents which had been exposed to heat from the cauterizer tip still appeared gold in color, indicating the presence of drug in the stent coating. The results above indicate that varying the amount of time and heat exposure can modify the elution rate of drug from the stent.

Example 15

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to compare the target coating formulation with the final coating formulation.

The results are as follows: For the primer layer, there was a target dry weight of 26 µg of polymer, and a measured average dry weight of 28±3 µg of polymer. For the reservoir layer, the target drug:polymer ratio was 1:1.25, and the measured average drug content was 128 µg. For the barrier layer, the measured average dry weight was 84 µg.

Example 16

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to compare the target coating formulation with the final coating formulation. The results are as follows: For the primer layer, there was a target dry weight of 26 µg of polymer, and a measured average dry weight of 28±2 µg of polymer. For the reservoir layer, the target drug:polymer ratio was 1:1.5, and the measured average drug content was 130 µg. For the barrier layer, the measured average dry weight was 81 µg.

After the solvent had been substantially removed and the coatings had been formed, a select number of stents were then heat treated by exposing the stents to a heat of 80° C. for 2 hours.

Example 17

The release rate of 40-O-(2-hydroxy)ethyl-rapamycin from the stents with coatings produced by the processes under Examples 15 and 16 were tested using the process described in Example 5. The following Table 6 summarizes the results of the release rate procedure for three stents from Example 15:

TABLE 6

| | Time (hrs) | | | | | | |
|---|---|---|---|---|---|---|---|
| | 3 | 6 | 9 | 12 | 24 | 32 | 48 |
| Cumulative Release from Stent 1 (µg) | 15.44 | 24.63 | 32.20 | 38.43 | 56.04 | 64.81 | 77.36 |
| Cumulative Release from Stent 2 (µg) | 12.70 | 21.29 | 28.57 | 34.55 | 51.19 | 59.27 | 71.15 |
| Cumulative Release from Stent 3 (µg) | 13.00 | 21.92 | 29.31 | 35.40 | 52.55 | 60.48 | 72.05 |

The following Table 7 summarizes the results of the release rate procedure for three stents from Example 16:

TABLE 7

| | Time (hrs) | | | | | | |
|---|---|---|---|---|---|---|---|
| | 3 | 6 | 9 | 12 | 24 | 32 | 48 |
| Cumulative Release from Stent 1 (µg) | 5.52 | 9.37 | 12.73 | 15.71 | 24.33 | 29.20 | 38.02 |

TABLE 7-continued

| | Time (hrs) | | | | | | |
|---|---|---|---|---|---|---|---|
| | 3 | 6 | 9 | 12 | 24 | 32 | 48 |
| Cumulative Release from Stent 2 (µg) | 6.73 | 10.86 | 14.39 | 17.41 | 25.99 | 30.29 | 38.00 |
| Cumulative Release from Stent 3 (µg) | 5.76 | 9.14 | 12.02 | 14.50 | 21.21 | 24.61 | 31.23 |

Figure 3:
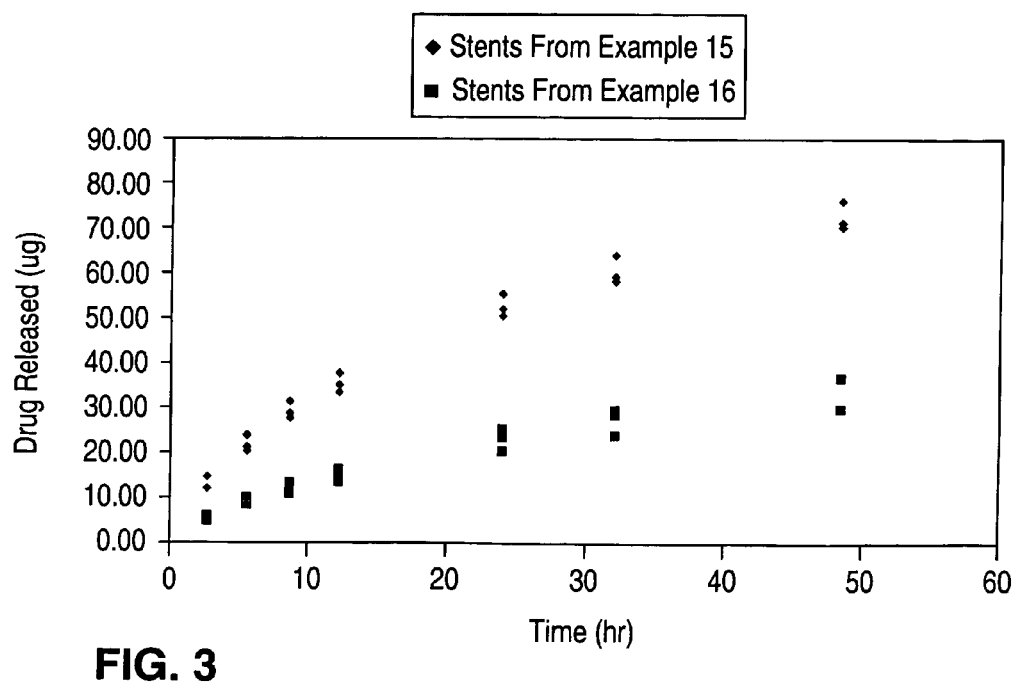

A comparison of the release rates for the stents from Examples 15-16 is graphically shown in FIG. 3. The results unexpectedly show that the stent coatings that were exposed to thermal treatment in Example 16 have a significantly lower release rate than the stent coatings of Example 15.

Example 18

This Example 18 is referred to as the "Porcine Serum Release Rate Procedure." A drug-coated stent was placed on a stent holder of a Vankel Bio-Dis release rate tester. The stent was dipped into porcine serum, with 0.1% sodium azide added, for 24 hrs. The stent was removed from the porcine serum and the drug solution analyzed by an HPLC procedure to determine how much drug was released into the porcine serum. The HPLC system consisted of a Waters 2690 system with an analytical pump, a column compartment (set at 40° C.), an auto-sampler, and a 996 PDA detector. The column was an YMC Pro C18 (150 mm×4.6 I.D., 3 µm particle size), maintained at a temperature of 40° C. The mobile phase consisted of 75% acetonitrile and 25% 20 mMolar ammonium acetate. The flow rate was set on 1 ml/min. The HPLC release rate results were quantified by comparing the results with a reference standard.

Example 19

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 µg of polymer, and a measured average dry weight of 45±1 µg of polymer. For the reservoir layer, the drug:polymer ratio was 1:1, and the measured average drug content was 151 µg as determined by Example 2. For the barrier layer, the measured average dry weight was 234 µg.

After the coatings were formed on the stents, a select number of stents were tested for the drug release rate from the coatings according to the procedure described in Example 18. It was determined that the average drug released in 24 hours was 32.6 µg, or 21.6% of the total.

Example 20

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 44±3 μg of polymer. For the reservoir layer, the drug:polymer ratio was 1:1.8, and the measured average drug content was 97 μg as determined by Example 2. For the barrier layer, the measured average dry weight was 184 μg.

After the coatings were formed on the stents, a select number of stents were tested for the drug release rate from the coatings according to the procedure described in Example 18. It was determined that the average drug released in 24 hours was 24.1 μg, or 24.8% of the total.

Example 21

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the tents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 41±1 μg of polymer. For the reservoir layer, the drug:polymer ratio was 1:1.8, and the measured average drug content was 227 μg as determined by Example 2. For the barrier layer, the measured average dry weight was 181 μg.

After the coatings were formed on the stents, a select number of stents were tested for the drug release rate from the coatings according to the procedure described in Example 18. It was determined that the average drug released in 24 hours was 27.5 μg, or 12.1% of the total.

Example 22

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. No barrier layer was applied for this Example.

A select number of stents were analyzed to quantify the coating components. For the primer layer, there was a target dry weight of 40 μg of polymer, and a measured average dry weight of 44±2 μg of polymer. For the reservoir layer, the drug:polymer ratio was 1:1.8, and the measured average drug content was 221 μg as determined by Example 2.

After the coatings were formed on the stents, a select number of stents were tested for the drug release rate from the coatings according to the procedure described in Example 18. It was determined that the average drug released in 24 hours was 129.4 μg, or 58.55% of the total.

Example 23

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 42 μg of polymer. For the reservoir layer, the drug:polymer ratio was 1:1.5, and the measured average drug content was 184 μg as determined by Example 2. For the barrier layer, the measured average dry weight was 81 μg.

After the coatings were formed on the stents, a select number of stents were tested for the drug release rate from the coatings according to the procedure described in Example 18. It was determined that the average drug released in 24 hours was 70.1 μg, or 38.1% of the total.

Example 24

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 45±1 μg of polymer. For the reservoir layer, the drug:polymer ratio was 1:1.75, and the measured average drug content was 200 μg as determined by Example 2. For the barrier layer, the measured average dry weight was 180 μg.

After the coatings were formed on the stents, a select number of stents were tested for the drug release rate from the coatings according to the procedure described in Example 18. It was determined that the average drug released in 24 hours was 39.0 μg, or 19.5% of the total.

Example 25

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 μg of polymer, and a measured average dry weight of 41±4 μg of polymer. For the reservoir layer, the drug:polymer ratio was 1:1, and the measured average drug content was 167 μg as determined by Example 2. For the barrier layer, the measured average dry weight was 184 μg.

After the coatings were formed on the stents, a select number of stents were tested for the drug release rate from the coatings according to the procedure described in Example 18. It was determined that the average drug released in 24 hours was 6.0 μg, or 3.6% of the total.

Example 26

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 26 μg of polymer, and a measured average dry weight of 24±2 μg of polymer. For the reservoir layer, the drug:polymer ratio was 1:1.25, and the measured average drug content was 120 μg as determined by Example 2. For the barrier layer, the measured average dry weight was 138 μg.

After the coatings were formed on the stents, a select number of stents were tested for the drug release rate from the coatings according to the procedure described in Example 18. It was determined that the average drug released in 24 hours was 11.0 μg, or 9.2% of the total.

Example 27

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of 1% (w/w) polybutylmethacrylate, 5.7% (w/w) acetone, 50% (w/w) xylene and 43.3% (w/w) HFE FLUX REMOVER (Techspray, Amarillo, Tex.). Another 2 hour bake at 50° C. was performed to remove the solvent.

A select number of stents were analyzed to quantify the coating components. For the primer layer, there was a target dry weight of 40 μg of polymer, and a measured average dry weight of 44±4 μg of polymer. For the reservoir layer, the drug:polymer ratio was 1:1, and the measured average drug content was 183 μg as determined by Example 2. For the barrier layer, the measured average dry weight was 168 μg.

After the coatings were formed on the stents, a select number of stents were tested for the drug release rate from the coatings according to the procedure described in Example 18. It was determined that the average drug released in 24 hours was 21.6 μg, or 11.8% of the total.

Example 28

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of 1% (w/w) polybutylmethacrylate, 5.7% (w/w) acetone, 50% (w/w) xylene and 43.3% (w/w) HFE FLUX REMOVER. Another 2 hour bake at 50° C. was performed to remove the solvent.

A select number of stents were analyzed to quantify the coating components. For the primer layer, there was a target dry weight of 40 μg of polymer, and a measured average dry weight of 41±2 μg of polymer. For the reservoir layer, the drug:polymer ratio was 1:1.8, and the measured average drug content was 102 μg as determined by Example 2. For the barrier layer, the measured average dry weight was 97 μg.

After the coatings were formed on the stents, a select number of stents were tested for the drug release rate from the coatings according to the procedure described in Example 18. It was determined that the average drug released in 24 hours was 9.1 μg, or 8.9% of the total.

Example 29

8 mm PIXEL stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of 1% (w/w) polybutylmethacrylate, 5.7% (w/w) acetone, 50% (w/w) xylene and 43.3% (w/w) HFE FLUX REMOVER (Techspray, Amarillo, Tex.). Another 2 hour bake at 50° C. was performed to remove the solvent.

A select number of stents were analyzed to quantify the coating components. For the primer layer, there was a target dry weight of 26 μg of polymer, and a measured average dry weight of 27±2 μg of polymer. For the reservoir layer, the drug:polymer ratio was 1:1.25, and the measured average drug content was 120 μg as determined by Example 2. For the barrier layer, the measured average dry weight was 68 μg.

After the coatings were formed on the stents, a select number of stents were tested for the drug release rate from the coatings according to the procedure described in Example 18. It was determined that the average drug released in 24 hours was 22.0 μg, or 18.3% of the total.

Example 30

A select number of stents from Example 3 were tested for the drug release rate from the coatings according to the procedure described in Example 18. It was determined that the average drug released in 24 hours was 22.8 μg, or 11.1% of the total.

Example 31

A select number of stents from Example 4 were tested for the drug release rate from the coatings according to the procedure described in Example 18. It was determined that the average drug released in 24 hours was 57.0 µg, or 20.2% of the total.

Example 32

Two stents were coated by spraying a 2% (w/w) solution of EVAL and 98% (w/w) dimethylacetamide to form a primer layer. For the primer layer, there was a target dry weight of 100 µg of polymer, and the measured dry weights were 93 µg and 119 µg, respectively. The two stents were then coated with an EVAL-40-O-(2-hydroxy)ethyl-rapamycin blend at a drug:polymer ratio of 2:1 to produce a reservoir layer. After application, it was determined that the reservoir layers had weights of 610 µg and 590 µg, respectively. From the total weight of the reservoir layers and the drug:polymer ratio, it was estimated that the coatings contained about 407 µg and 393 µg of 40-O-(2-hydroxy)ethyl-rapamycin, respectively. Polymeric barrier layers were also applied to the stents and it was determined that the weights of the barrier layers were 279 µg and 377 µg, respectfully.

The stents from this Example were then sterilized using an ethylene oxide sterilization process. In particular, the stents were placed in a chamber and exposed to ethylene oxide gas for 6 hours at 130-140° F., with a relative humity of 45-80%. The stents were then aerated for about 72 hours at 110-130° F.

Figure 4:
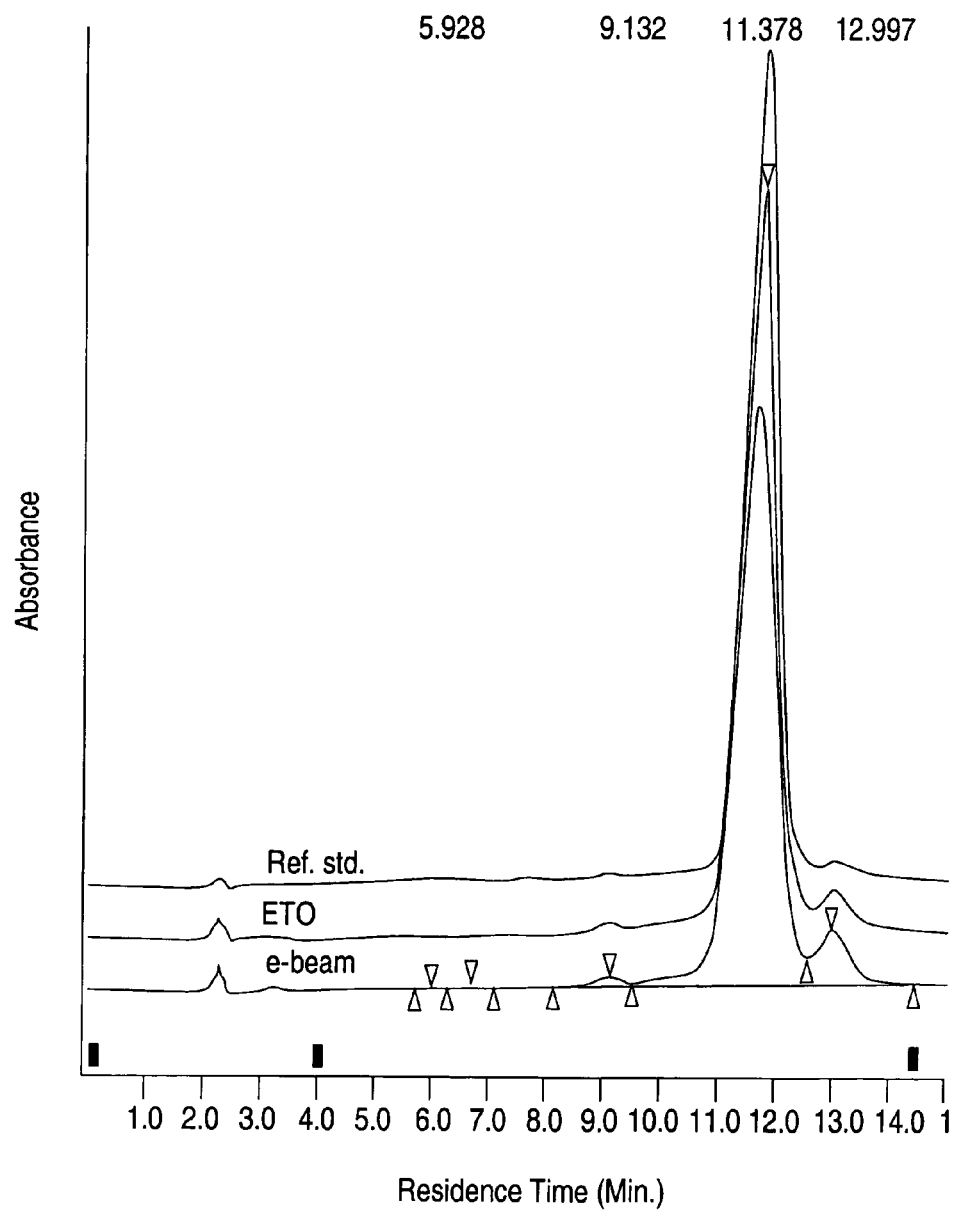
FIG. 4 is a chromatograph as referred to in Examples 32 and 33.

After sterilization, the coatings were then analyzed using an HPLC to determine the peak purity of the drug in the stent coatings. It was determined that the 40-O-(2-hydroxy)ethyl-rapamycin in the coatings had peak purities of about greater than 95%. FIG. 4 is a chromatograph showing the peak purity the 40-O-(2-hydroxy)ethyl-rapamycin in one of the coatings, labeled "ETO," as compared to a reference standard for 40-O-(2-hydroxy)ethyl-rapamycin, labeled "Ref. Std."

Example 33

Two stents were coated by spraying a 2% (w/w) solution of EVAL and 98% (w/w) dimethylacetamide to form a primer layer. For the primer layer, there was a target dry weight of 100 µg of polymer, and the measured dry weights were 99 µg and 94 µg, respectively. The two stents were then coated with an EVAL-40-O-(2-hydroxy)ethyl-rapamycin blend at a drug:polymer ratio of 2:1 to produce a reservoir layer. After application, it was determined that the reservoir layers had weights of 586 µg and 588 µg, respectively. From the total weight of the reservoir layers and the drug:polymer ratio, it was estimated that the coatings contained about 391 µg and 392 µg of 40-O-(2-hydroxy)ethyl-rapamycin, respectively. Polymeric barrier layers were also applied to the stents and it was determined that the weights of the barrier layers were 380 µg and 369 µg, respectfully.

The stents from this Example were then sterilized using an e-beam sterilization process. In particular, the stents were placed in a stent container which was run through an e-beam chamber. While moving through the e-beam chamber via a conveyor belt, the stent container was exposed to an e-beam with a constant energy level so that the stent container received between 33.11 and 46.24 KGy. The stent therefore at any point along the length of the stent received at a minimum 25 KGy.

After sterilization, the coating was then analyzed using an HPLC to determine the peak purity of the drug in the stent coating. It was determined that the 40-O-(2-hydroxy)ethyl-rapamycin in the coating had a peak purity of about greater than 95%. FIG. 4 is a chromatograph showing the peak purity the 40-O-(2-hydroxy)ethyl-rapamycin in one of the coatings, labeled "e-beam," as compared to a reference standard for 40-O-(2-hydroxy)ethyl-rapamycin, labeled "Ref. Std."

Example 34

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 µg of polymer, and a measured average dry weight of 44±3 µg of polymer. For the reservoir layer; the drug:polymer ratio was 1:2, and the measured average drug content was 245 µg as determined by Example 2. For the barrier layer, the measured average dry weight was 104 µg.

After the coatings were formed on the stents, a select number of stents were tested for the drug release rate from the coatings according to the procedure described in Example 18. It was determined that the average drug released in 24 hours was 23.5 µg, or 9.6% of the total.

Example 35

13 mm PENTA stents were coated by spraying a 2% (w/w) solution of EVAL and 98% (w/w) dimethylacetamide. The solvent was removed by baking at 140° C. for 2 hours. A solution of EVAL and 40-O-(2-hydroxy)ethyl-rapamycin in a mixture of 70% (w/w) dimethylacetamide and 30% (w/w) ethanol was spray coated onto the stents. The stents were then baked at 50° C. for 2 hours. A barrier layer was formed by spraying the stents with a solution of EVAL in a mixture of 80% (w/w) dimethylacetamide and 20% (w/w) pentane. Another 2 hour bake at 50° C. was performed to remove the solvent.

A select number of stents were analyzed to quantify the coating components. For the primer layer, there was a target dry weight of 40 µg of polymer, and a measured average dry weight of 45±3 µg of polymer. For the reservoir layer, the drug:polymer ratio was 1:1.5, and the measured average drug content was 337 µg as determined by Example 2. For the barrier layer, the measured average dry weight was 169 µg.

After the coatings were formed on the stents, a select number of stents were tested for the drug release rate from the coatings according to the procedure described in Example 18. It was determined that the average drug released in 24 hours was 37.1 µg, or 11.0% of the total.

Example 36

Figure 5:
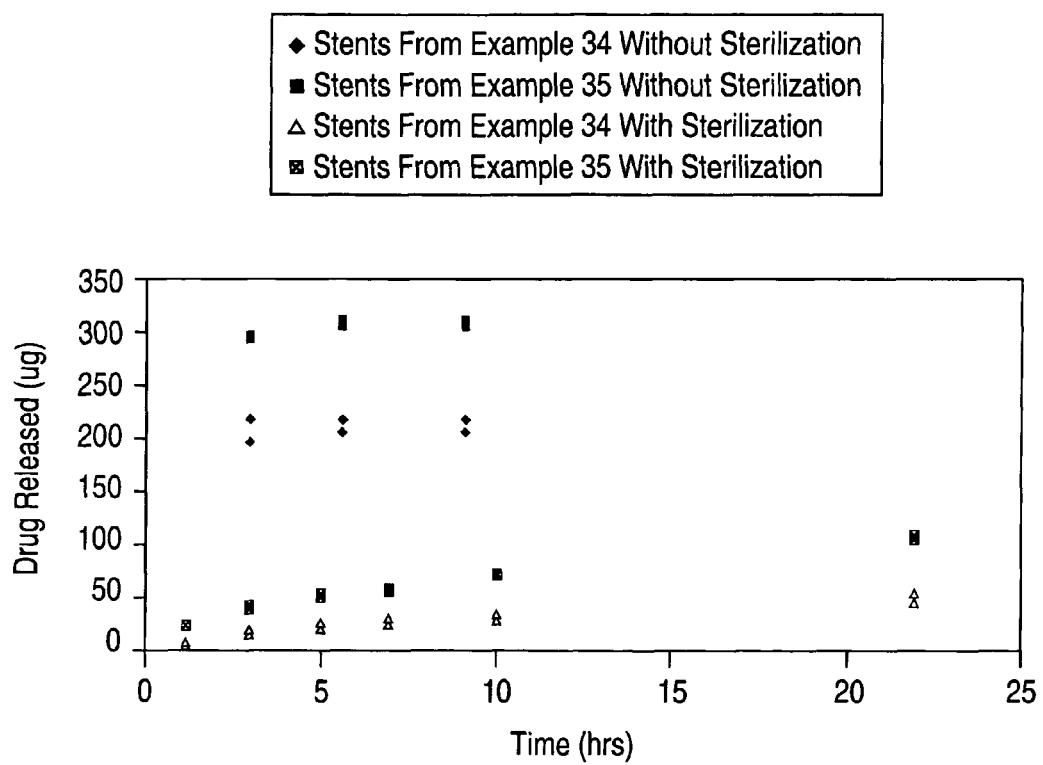
FIG. 5 is a graph showing the release rate of 40-O-(2-hydroxy)ethyl-rapamycin from stent coatings in accordance with an embodiment of the present invention.

Stents from Example 34 and stents from Example 35 were sterilized according to the process described in Example 32. The released rates of the drug in the stent coatings of sterilized stents and non-sterilized were then tested according to the process described in Example 5. The results of the release rate test are graphically shown in FIG. 5.

Example 37

A 13 mm PENTA stent can be coated by spraying a solution of EVAL, 40-O-(2-hydroxy)ethyl-rapamycin and ethanol onto the stent. The stent is then baked at 50° C. for 2 hours to yield a reservoir coating with 300 µg of EVAL and 300 µg of 40-O-(2-hydroxy)ethyl-rapamycin. A barrier layer can be formed by spraying the stent with a solution of EVAL and pentane. A second 2 hour bake at 50° C. can be performed to remove the solvent to yield a barrier coating with 320 µg of EVAL.

Example 38

A 13 mm PENTA stent can be coated by spraying a solution of EVAL and DMAC onto the stent. The solvent is removed by baking at 140° C. for 2 hours to yield a primer coating with 100 µg of EVAL. A reservoir layer can be applied by spraying a solution of EVAL, 40-O-(2-hydroxy)ethyl-rapamycin and ethanol onto the stent. The stent is then baked at 50° C. for 2 hours to yield a reservoir coating with 200 µg of EVAL and 400 µg of 40-O-(2-hydroxy)ethyl-rapamycin. A barrier layer can be formed by spraying the stent with a solution of EVAL and pentane. A second 2 hour bake at 50° C. is performed to remove the solvent to yield a barrier coating with 350 µg of EVAL.

Example 39

A 13 mm PENTA stent can be coated by spraying a solution of EVAL, 40-O-(2-hydroxy)ethyl-rapamycin and ethanol onto the stent. The stent is then baked at 50° C. for 2 hours to yield a reservoir coating with 500 µg of EVAL and 250 µg of 40-O-(2-hydroxy)ethyl-rapamycin. A barrier layer can be formed by spraying the stent with a solution of EVAL and pentane. A second 2 hour bake at 50° C. is performed to remove the solvent to yield a barrier coating with 300 µg of EVAL.

Example 40

A 13 mm PENTA stent can be coated by spraying a solution of EVAL, 40-O-(2-hydroxy)ethyl-rapamycin and ethanol onto the stent. The stent is then baked at 50° C. for 2 hours to yield a reservoir coating with 475 µg of EVAL and 175 µg of 40-O-(2-hydroxy)ethyl-rapamycin. A barrier layer can be formed by spraying the stent with a solution of EVAL and pentane. A second 2 hour bake at 50° C. is performed to remove the solvent to yield a barrier coating with 300 µg of EVAL.

Example 41

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 400 µg of EVAL and 200 µg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 300 µg of EVAL.

Example 42

An 8 mm Pixel stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 400 µg of EVAL and 200 µg of 40-O-(2-hydroxy)ethyl-rapamycin. A barrier layer can be formed by spraying the stent with a solution of polybutylmethacrylate ("PBMA") and HFE FLUX REMOVER. A second 2 hour bake at 50° C. is performed to remove the solvent to yield a barrier coating with 150 µg of PBMA.

Example 43

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 µg of EVAL and 200 µg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 200 µg of EVAL.

Example 44

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 µg of EVAL and 200 µg of 40-O-(2-hydroxy)ethyl-rapamycin. A barrier layer can formed by spraying the stent with a solution of PBMA and HFE FLUX REMOVER. A second 2 hour bake at 50° C. is performed to remove the solvent to yield a barrier coating with 150 µg of PBMA.

Example 45

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 µg of EVAL and 200 µg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 200 µg of EVAL.

Example 46

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 µg of EVAL and 200 µg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 100 µg of PBMA.

Example 47

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 270 µg of EVAL and 150 µg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 150 μg of EVAL.

Example 48

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 170 μg of EVAL and 150 μg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 75 μg of PBMA.

Example 49

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 150 μg of EVAL and 150 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 200 μg of EVAL. A finishing layer can then applied by spraying the stent with a solution of EVAL, polyethyleneoxide (molecular weight of 17.5 K) ("PEO") and dimethylacetamide. The stent is baked at 50° C. for 2 hours to remove the solvent to yield a finishing coating with 83 μg of EVAL and 17 μg of PEO.

Example 50

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 270 μg of EVAL and 150 μg of 40-O-(2-hydroxy)ethyl-rapamycin. A barrier layer can formed by spraying the stent with a solution of EVAL and a mixture of dimethylacetamide and pentane. A second 2 hour bake at 50° C. is performed to remove the solvent to yield a barrier coating with 150 μg of EVAL. A finishing layer can then applied by spraying the stent with a solution of EVAL, PEO and dimethylacetamide. The stent is baked at 50° C. for 2 hours to remove the solvent to yield a finishing coating with 83 μg of EVAL and 17 μg of PEO.

Example 51

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 μg of EVAL and 200 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 100 μg of EVAL.

Example 52

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 200 μg of EVAL and 200 μg of 40-O-(2-hydroxy)ethyl-rapamycin. A barrier layer can be formed by spraying the stent with a solution of EVAL, KYNAR and HFE FLUX REMOVER. A second 2 hour bake at 50° C. is performed to remove the solvent to yield a barrier coating with 50 μg of EVAL and 50 μg of KYNAR.

Example 53

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 350 μg of EVAL and 200 μg of 40-O-(2-hydroxy)ethyl-rapamycin. A barrier layer is formed by spraying the stent with a solution of EVAL and a mixture of dimethylacetamide and pentane. A second 2 hour bake at 50° C. is performed to remove the solvent to yield a barrier coating with 200 μg of EVAL.

Example 54

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 350 μg of EVAL and 200 μg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 10.0 μg of PBMA.

Example 55

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 350 μg of EVAL and 200 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 200 μg of EVAL.

Example 56

An 8 mm PIXEL stent is coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 350 μg of EVAL and 200 μg of 40-O-(2-hydroxy)ethyl-rapamycin. A barrier layer can be formed by spraying the stent with a solution of EVAL and a mixture of dimethylacetamide and pentane. A second 2 hour bake at 50° C. is performed to remove the solvent to yield a barrier coating with 100 μg of EVAL. A finishing layer can then be applied by spraying the stent with a solution of EVAL, PEO and dimethylacetamide. The stent is baked at 50° C. for 2 hours to remove the solvent to yield a finishing coating with 83 μg of EVAL and 17 μg of PEO.

Example 57

An 8 mm PIXEL stent can be coated by spraying a solution of EVAL and 40-O-(2-hydroxy)ethyl-rapamycin in a mixture of dimethylacetamide and ethanol onto the stent. The stent is then baked at 50° C. for 2 hours to yield a reservoir coating with 350 µg of EVAL and 200 µg of 40-O-(2-hydroxy)ethyl-rapamycin. A barrier layer can be formed by spraying the stent with a solution of PBMA and HFE FLUX REMOVER. A second 2 hour bake at 50° C. is performed to remove the solvent to yield a barrier coating with 75 µg of PBMA. A finishing layer can then be applied by spraying the stent with a solution of PBMA, PEO and dimethylacetamide. The stent is baked at 50° C. for 2 hours to remove the solvent to yield a finishing coating with 62.5 µg of PBMA and 12.5 µg of PEO.

While particular embodiments of the present invention have been shown and described, it will be obvious to those skilled in the art that changes and modifications can be made without departing from this invention in its broader aspects.

What is claimed is:

1. A method of treating a coating, including a polymer, on a stent to reduce the rate of release of 40-O-(2-hydroxy)ethyl-rapamycin from the coating, comprising:

exposing the coating to a temperature, between the glass transition temperature and the melting temperature of the polymer, that causes modifications in the structure of the polymer which allows for the reduction of the release rate of the 40-O-(2-hydroxy)ethyl-rapamycin through the polymer, wherein the amount of the 40-O-(2-hydroxy)ethyl-rapamycin-released in 24 hours after the implantation of the stent in a blood vessel of a human being is less than about 50% of the total amount of 40-O-(2-hydroxy)ethyl-rapamycin contained in the coating; and maintaining the peak purity of the 40-O-(2-hydroxy)ethyl-rapamycin to greater than 90%.

2. The method of claim 1, wherein the coating includes an additive for shifting the glass transition temperature and/or the melting temperature of the polymer to a temperature different than the glass transition temperature or the melting temperature of the polymer without the additive.

3. The method of claim 2, wherein the additive is dioctyl phthalate.

4. The method of claim 2, wherein the amount of the additive included in the coating shifts the polymer glass transition temperature and/or the polymer melting temperature thus allowing for the temperature exposure without degradation of the 40-O-(2-hydroxy)ethyl-rapamycin or the polymer.

* * * * *

UNITED STATES PATENT AND TRADEMARK OFFICE
CERTIFICATE OF CORRECTION

PATENT NO. : 8,173,199 B2  Page 1 of 1
APPLICATION NO. : 11/527893
DATED : May 8, 2012
INVENTOR(S) : Syed F. A. Hossainy et al.

It is certified that error appears in the above-identified patent and that said Letters Patent is hereby corrected as shown below:

IN THE SPECIFICATIONS:

In Column 3, please delete the paragraph from line 64 to line 67:

"Examples of analogs or derivatives of 40-O-(2-hydroxy)ethyl-rapamycin include but are not limited to 40-O-(2-hydroxy)propyl-rapamycin and 40-O-(2-hydroxy)ethoxy]ethyl-rapamycin."

And insert the following paragraph:

--Examples of analogs or derivatives of 40-O-(2-hydroxy)ethyl-rapamycin include but are not limited to 40-O-(3-hydroxy)propyl-rapamycin and 40-O-[2-(2-hydroxy)ethoxy]ethyl-rapamycin.--

Signed and Sealed this
Second Day of October, 2012

David J. Kappos
*Director of the United States Patent and Trademark Office*